US008273581B2

(12) United States Patent
Schabron et al.

(10) Patent No.: US 8,273,581 B2
(45) Date of Patent: *Sep. 25, 2012

(54) PROCESSING AND ANALYSIS TECHNIQUES INVOLVING IN-VESSEL MATERIAL GENERATION

(75) Inventors: John F. Schabron, Laramie, WY (US); Joseph F. Rovani, Jr., Laramie, WY (US)

(73) Assignee: The University of Wyoming Research Corporation, Laramie, WY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/243,782

(22) Filed: Sep. 23, 2011

(65) Prior Publication Data
US 2012/0016168 A1  Jan. 19, 2012

Related U.S. Application Data

(63) Continuation of application No. 12/970,535, filed on Dec. 16, 2010, which is a continuation of application No. 11/510,491, filed on Aug. 25, 2006, now Pat. No. 7,875,464.

(60) Provisional application No. 60/711,599, filed on Aug. 25, 2005.

(51) Int. Cl.
*G01N 1/22* (2006.01)
*G01N 1/18* (2006.01)
*B01D 15/08* (2006.01)
*C02F 1/28* (2006.01)
*C07C 13/00* (2006.01)

(52) U.S. Cl. ........ 436/181; 436/178; 210/635; 210/656; 585/20

(58) Field of Classification Search .................. 436/181
See application file for complete search history.

(56) References Cited

U.S. PATENT DOCUMENTS

| 4,493,765 A | 1/1985 | Long et al. |
| 4,628,204 A | 12/1986 | Maes |
| 4,634,680 A | 1/1987 | Kingsley |
| 4,865,741 A | 9/1989 | Nolte et al. |
| 4,988,446 A | 1/1991 | Haberman et al. |
| 4,990,773 A | 2/1991 | Supernaw et al. |

(Continued)

FOREIGN PATENT DOCUMENTS

EP  400989 A  5/1990

(Continued)

OTHER PUBLICATIONS

"Energy and Environmental Profile of the US Petroleum Refining Industry," 1988, Prepared by Energetics Inc. for U.S. Department of Energy Office of Industrial Technologies, pp. 4-5, 27, 33, 49 and 62-63.

(Continued)

*Primary Examiner* — In Suk Bullock
*Assistant Examiner* — Bryan Kilpatrick
(74) *Attorney, Agent, or Firm* — Santangelo Law Offices, P.C.

(57) ABSTRACT

In at least one embodiment, the inventive technology relates to in-vessel generation of a material from a solution of interest as part of a processing and/or analysis operation. Preferred embodiments of the in-vessel material generation (e.g., in-vessel solid material generation) include precipitation; in certain embodiments, analysis and/or processing of the solution of interest may include dissolution of the material, perhaps as part of a successive dissolution protocol using solvents of increasing ability to dissolve. Applications include, but are by no means limited to estimation of a coking onset and solution (e.g., oil) fractionating.

75 Claims, 22 Drawing Sheets

U.S. PATENT DOCUMENTS

| | | | |
|---|---|---|---|
| 5,092,983 | A | 3/1992 | Eppig et al. |
| 5,574,215 | A | 11/1996 | Bunger et al. |
| 5,861,228 | A | 1/1999 | Descales et al. |
| 5,969,237 | A | 10/1999 | Jones et al. |
| 6,773,921 | B1 | 8/2004 | Schabron et al. |
| 7,875,464 | B2 | 1/2011 | Schabron et al. |
| 2003/0211621 | A1 | 11/2003 | Rovani et al. |
| 2011/0062058 | A1 | 3/2011 | Rogel et al. |
| 2011/0066441 | A1 | 3/2011 | Ovalles et al. |
| 2011/0120950 | A1 | 5/2011 | Schabron et al. |
| 2012/0160015 | A1 | 6/2012 | Ovalles et al. |

FOREIGN PATENT DOCUMENTS

| | | | |
|---|---|---|---|
| WO | 0077120 | A2 | 12/2000 |
| WO | 0077120 | A3 | 12/2000 |
| WO | 02063292 | A1 | 8/2002 |
| WO | 03096011 | A1 | 11/2003 |
| WO | 2011032123 | A2 | 3/2011 |
| WO | 2011032125 | A2 | 3/2011 |
| WO | 2011113017 | A2 | 9/2011 |

OTHER PUBLICATIONS

"Standard Test Method for Molecular Weight (Relative Molecular Mass) of Hydrocarbons by Thermoelectric Measurement of Vapor Pressure," ASTM Designation: D 2503-82 (Reapproved 1997), 871-873.

Andersen, S.I. et al., 1991, "Aggregation of Asphaltenes as Determined by Calorimetry," Journal of Colloid and Interface Science, 142, 497-502, 1991.

Barton, A.F., 1974, "Solubility Parameters," Chemical Reviews, 75 (6), 731-753.

Bodusynski, M.M. et al., 1982, •Separation of Solvent-Refined Coal into Solvent-Derived Fractions, Analytical Chemistry, 54, 372-375.

Burrell, H., 1955, •Solubility Parameters.• Interchemical Review, 3-16.

Carrier, H. et al; •Acoustic method for measuring asphaltene flocculation in crude oils•, Journal of Petroleum Science and Engineering, pp. 111-117.

Cartz, L., ch. 3, •Ultrasonic Testing•, Nondestructive Testing, 1995, pp. 81-98.

Del Bianco, A. et al., 1993, Thermal Cracking of Petroleum Residues 1. Kinetic Analysis of the Reaction. Fuel, 72 (1), 75•80.

Heithaus, J.J., 1962, •Measurement and Significance of Asphaltene Peptization.• Journal of the Institute of Petroleum 48 (458), 45-53.

Hildebrand, J.H. et al., 1970, •Regular and Related Solutions,• Van Nostrand Reinhold, NY, pp. 24-27, pp. 152-153, pp. 212-215.

Jones et al. •Development of an ultrasonic oil stability monitor for the assessment of asphaltene aggregation in hydrocarbon streams•, Proceed. Intern. Conf. Mitigat. Heat Exch. Foul. Econ. Envir. Implic. Banff, AB, Canada, Jul. 1999, 84-94.

Long, R.B. et al., 1989, •Studies in Petroleum Composition,• Revue del•Institute Francais du Petrole, abstract.

Long, R.B., 1979, •The Concept of Asphaltenes,• Preprints, Div. Petroleum Chemistry, American Chemical Society, 24, 891-901.

Magaril, R.Z. et al., 1968, Study of the Mechanism of Coke Formation in the Cracking of Petroleum Resins, International Chemical Engineering 8 (4), 727.

McClements, D.J., •Ultrasonic Measurements in Particle Size Analysis•, University of Massachusetts, Amherst, USA, Encyclopedia of Analytical Chemistry (Applications, Theory and Instrumentation) pp. 5581-5587.

Pal R. et al., 1989, Viscosity/Concentration Relationships for Emulsions. Journal of Rheology, 33 (7), 1021-1045.

Pauli, A.T. 1996, •Asphalt Compatibility Testing Using the Automated Heithaus Titration Test,• Preprints, Division of Fuel Chemistry, American Chemical Society, 41 (4), 1276-1281.

Pauli, A.T. et al., 1998, Relationships Between Asphaltenes, Heithaus Compatibility Parameters, and Asphalt Viscosity. Petrol. Science and Technology, 16 (9&10), 1125-1147.

Pauli, A.T. et al., •Stability and Compatibility Testing of Petroleum and Asphalt,• American Laboratory, Sep. 2003, 2 pages.

Phillips, C.R, et al. 1985, Kinetic Models for the Thermal Cracking of Athabaska Bitumen, Fuel 64(5), 678-691.

Scatchard, G. 1931, •Equilibria in Non-Electrolyte Solutions in Relation to the Vapor Pressure and Densities of the Components,• Chemical Reviews, 321-333.

Schabron, J.F. et al. •Coking indexes using the Heithaus titration and asphaltene solubility., Preprints • American Chemical Society, Division of Petroleum Chemistry (1999), 44(2), 187-189.

Schabron, J.F. et al., 1998, •The Solubility and Three-Dimensional Structure of Asphaltenes,• Petroleum Science and Technology, 16 (3-4), 361-376.

Schabron, J.F. et al., 1999 •Petroleum Residua Solubility Parameter/Polarity Map: Stability Studies of Residua Pyrolysis,• Department of Energy Report under contract # DE-FC26-98FT40322 Task, 1.2, 24 pages.

Schabron, J.F. et al., 2000 •Deposition from Heavy Oils,• Department of Energy Report under contract # DE-FC26-98FT40322, 35 pages.

Schabron, J.F. et al., 2001b, Molecular Weight / Polarity Map for Residua Pyrolysis, Fuel, 80 (4), 529-537.

Schabron, J.F. et al., 2001c, Non-Pyrolytic Heat Induced Deposition from Heavy Oils, Fuel, 80 (7) 919-928.

Schabron, J.F., et al., 2002b, Residua Coke Formation Predictability Maps, Fuel, 81 (17) 2227-2240.

Schabron, J.F. et al., 2001a, Predicting Coke Formation Tendencies, Fuel, 80 (10) 1435-1446.

Schabron, J.F. et al., 2002a, Characterization of Residua During Pyrolysis, Preprints, Div. of Petroleum Chemistry, American Chemical Society, 47 (1), 17-21.

Schabron, J.F. et al., 1993, •The Characterization of Petroleum Residua,• U.S. Dept of Energy Report under contract # DE-FC21-86MC11076I, 68 pages.

Schabron, J.F. et al., 2002, •Thermal Analysis for Monitoring Incipient Coke Formation•, US Department of Energy Report DE/FG36/01G011018, 18 pages.

Schabron, J.F. et al , 2002, •Coke Formation Process Model for Petroleum Refining Efficiency Improvement•, US Department of Energy Report under contract # DE/FG36/01G011018, 40 pages.

Schabron, J.F. et al., 2004, Refinery Efficiency Improvement Ultrasonic Spectroscopy and WRI Coking Indexes, WRI Report 04-R009 to DOE under Cooperative Agreement DE-FC26-98FT40322.

Singh, I.D., V. Kothiyal, V. Ramaswamy, and R. Krishna, 1990, Characteristic Changes of Asphaltenes During Visbreaking of North Gujarat Short Residue. Fuel, 69 (3), 289•292.

Small, P.A., 1953, •Some Factors Affecting the Solubility of Polymers,• Journal of Applied Chemistry, 71-80.

Snyder, L.R., 1968, •Principles of Adsorption Chromatography,• Marcel Dekker, Inc., New York, 206-210.

Wiehe, I.A., 1993, A Phase-Separation Kinetic Model for Coke Formation, Ind. Eng. Chem. Res., 32 (11), 2447•2454.

Wiehe, I.A., 1996, •Two-Dimensional Solubility Parameter Mapping of Heavy Oils,• Fuel Science and Technology International, 14 (1&2), 289-312.

Bodusynski, M.S. et al., 1987, "Composition of heavy petroleums: 1. molecular weight, hydrogen deficiency, and heteroatom concentration as a function of atmospheric equivalent boiling point up to 1400 degrees F" Energy & Fuels, 1, 2-11.

Schabron, J.F., et al., 2006, "Initial studies using ultrasonic spectroscopy for monitoring changes in residua with pyrolysis," Fuel 85, 2093-2105.

Phillips, C.R., et al., 1985, Kinetic Models for the Thermal Cracking of Athabaska Bitumen, Fuel 64 (5), 678-691.

Chiantore, Oscar and Simonelli, Alessandra, "Precipitation-redissolution Liquid Chromatography of Styrene-ethyl Acrylate Copolymers," Polymer Engineering and Science, Aug. 1999, vol. 39 No. 8, p. 1383-1388.

Cortell, Jessica M. et al., "Infulence of Vine Vigor on Grape (Vitis vinifera L. Cv. Pino Noir) Anthrocyanins. 2. Anthocyanins and Pigmented Polymers in Wine," J. Agric. Food Chem. 2007, 55, p. 6585-6595.

Aske, Narve et al.; "Determination of Saturate, Aromatic, Resin, and Asphaltenic (SARA) Components in Crude Oils by Means of Infrared and Near-Infrared Spectroscopy," Energy & Fuels, 2001, 15, 1304-1312.

Corbett, L.W., "Composition of Asphalt Based on Generic Fractionation, Using Solvent Deasphaltening, Elution-Adsorption Chromatography, and Densimetric Characterization," Analytical Chemistry, p. 576.

McCarthy, James E. et al.; "EPA's Regulation of Coal-Fired Power: Is a "Train Wreck" Coming?", Congressional Research Service, CRS Report for Congress, Aug. 8, 2011, Jul. 5700, R41914.

"Standard Test Method for n-Heptane Insulbles1", Designation: D 3279-97 (Reapproved 2001).

"Standard Test Method for Separation of Asphalt into Four Fractions1," ASTM International, Designation D4124-09.

"Energy and Environmental Profile of the US Petroleum Refining Industry," 1988, Prepared by Energetics Inc. For U.S. Department of Energy Office of Industrial Technologies.

Schabron, J.F., et al., "Asphaltene Determinator Method for Automated On-Column Precipitation and Redissolution of Pericondensed Aromatic Asphaltene Components," Energy Fuels 2010, 24, 5984-5996.

Fan, T. et al., "Rapid and Accurate SARA Analysis of Medium Gravity Crude Oils," Energy & Fuels 2002, 16, 1571-1575.

Schabron, J.F., et al., "On-column precipitation and re-dissolution of asphaltenes in petroleum residua," Fuel 87 (2008) 165-176.

Grizzle, Patrick L, et al., "Automated Liquid Chromatographic Compound Class Grou-Type Separation of Crude Oils and Bitumens Using Chemically Bonded Aminosilane," Anal. Chem. 1986, 58, 2389-2396.

Jewell, D.M. et al., "Ion-Exchange, Coordination, and Adsorption Chromatographic Separation of Heavy-End Petroleum Distillates," Laramie Energy Research Center, Analytical Chemistry, vol. 44, No. 8, Jul. 1972, p. 1391.

Jiang, C et al., "TLC-FID (latroscan) analysis of heavy oil and tar sand samples," Organic Geochemistry 39 (2008) 1210-1214.

Karlsen, D.A. et al., "Analysis of petroleum fractions by TLC-FID: applications to petroleum reservoir description," Org. Geochem. vol. 17, No. 5, pp. 603-617, 1991.

Kharrat, A. et al., "Issues with Comparing SARA Methodologies," Energy & Fuels 2007, 21, 3618-3621.

Masson, J-F et al., "Dynamics of Bitumen Fractions by Thin-Layer Chromatography/Flame Ionization Detection," Energy & Fuels 2001, 15, 955-960.

Radke, M et al., "Preparative Hydrocarbon Group Type Determination by Automated Medium Pressure Liquid Chromatography," Anal. Chem. 1980, 52, 406-411.

Schabron, J.F. et al.; "Petroleum Processing Efficiency Improvement," Topical Report, May 2011.

Wiehe, Irwin A. et al.; "The Oil Compatibility Model and Crude Oil Incompatibility," Energy & Fuels 2000, 14, 56-59.

Fan, Z et al.; "Challenges in Processing Bitumens and Heavy Oils," Prepr. Pap.-Am. Chem. Soc., Div. Petr. Chem. 2009, 54 (1), 4.

"Canada regulator approves Enbridge diluent Line," Reuters, Business & Financial News, Feb. 19, 2008, Calgary, Alberta.

"Opportunity Crudes Report II: Technologies and Strategies for Meeting Evolving Market and Environmental Challenges," Hydrocarbon Publishing Company, an updated and expanded study of the 2006 report titled "Opportunity Crudes: Technical Challenges and Economic Benefits.".

http://www.specialchem4adhesives.com/resources, Determining Critical Surface Tension of Solid Substrates, printed Sep. 13, 2011, 3 pages.

Energy Information Administration/Capacity Report 2001.

Robinson, P. R., Petroleum Processing Overview, Practical Advances in Petroleum Processing 2006:1-78.

Rogel, E. et al. Asphaltene Stability in Processed Samples using Solubility Profile Analysis, Prepr. Pap.-Am. Chem. Soc. Div. Pet. Chem. 2011, 56(1), 3.

Ovalles, C. et al. Characterization and Preparative Separation of Heavy Crude Oils, their fractions and thermally Cracked Products by the Asphaltene solubility Fractions Method, Prepr. Pap.-Am. Chem. Soc. Div. Pet. Chem. 2011, 56(1), 8.

Schabron J. F. et al., Total Pericondensed Aromatic (TPA) Determination as an Alternative to Gravimetric Asphaltenes, Prepr. Pap.-Am. Chem. Soc. Div. Pet. Chem. 20011, 56(1), 38.

Rogel, E. et al. Determination of Asphaltenes in Crude Oil and Petroleum Products by the on column Precipitation Method, Energy Fuels 2009, 23, 4515-4521.

Ovalles, C. et al. Characterization of Heavy Crude Oils, Their Fractions, and Hydrovisbroken Products by the Asphaltene Solubility Fraction Method, dx.doi.org/10.1021/ef201499f | Energy Fuels 2012, 26, 549-556, Published: Dec. 7, 2011.

Lopez-Linares, F. et al. Adsorption of Athabasca Vacuum Residues and Their Visbroken Products over Macroporous Solids: Influence of Their Molecular Characteristics, dx.doi.org/10.1021/ef201047z | Energy Fuels 2011, 25, 4049-4054, Published Aug. 17, 2011.

Rogel, E., Asphaltene Chemical Characterization as a Function of Solubility: Effects on Stability and Aggregation, dx.doi.org/10.1021/ef2013979 | Energy Fuels, Published Nov. y7, 2011.

Schabron, J. F. et al. The Waxphaltene Determinator Method for Automated Precipitation and Re-Dissolution of Wax and Asphaltene Components, Energy Fuels, Article ASAP, Doi: 10.1021/ef300184s, Feb. 27, 2012.

Parallel U.S. Appl. No. 12/970,535, Notice of Allowance dated Jun. 8, 2012.

Parallel U.S. Appl. No. 13/490,316; Office action dated Aug. 3, 2012.

PROCESSING AND ANALYSIS TECHNIQUES INVOLVING IN-VESSEL MATERIAL GENERATION

PRIORITY CLAIM

This application is a continuation application of, and claims benefit of and priority to, U.S. patent application Ser. No. 12/970,535, filed on Dec. 16, 2010 (published as publication number US 20110120950 A1 on May, 26, 2011) which itself is a continuation application of, and claims benefit of and priority to, U.S. patent application Ser. No. 11/510,491, filed Aug. 25, 2006 (published as publication number US 2007/0048874 A1 on Mar. 1, 2007 and issued as U.S. Pat. No. 7,875,464 B2 on Jan. 25, 2011) which itself is a United States non-provisional patent application and claims benefit of and priority to U.S. provisional patent application Ser. No. 60/711,599, filed Aug. 25, 2005, each said application hereby incorporated herein by reference in its entirety.

GOVERNMENT LICENSE RIGHTS

This application relates to work performed under US DOE Cooperative Agreement DE-FC26-98FT40322. The US government may have certain rights in this inventive technology, including "march-in" rights, as provided for by the terms of US DOE Cooperative Agreement DE-FC26-98FT40322.

BACKGROUND OF THE INVENTION

Generally, this inventive technology relates to substance analysis and/or processing. More specifically, the inventive technology, in at least one embodiment, relates to in-vessel generation of a material from a solution of interest as part of a processing and/or analysis operation. Preferred embodiments of the in-vessel material generation (e.g., in-vessel solid material generation) include precipitation; in certain embodiments, analysis and/or processing of the solution of interest may include dissolution of the material, perhaps as part of a successive dissolution protocol using solvents of increasing ability to dissolve the material, in order to gain a desired amount of information about the solution of interest or to process a solution of interest as desired. Applications include, but are by no means limited to estimation of a coking onset and solution (e.g., oil) fractionating.

SUMMARY OF THE INVENTION

The present inventive technology includes a variety of aspects which may be selected in different combinations based upon the particular application or needs to be addressed. In one basic form, the inventive technology relates to in-vessel generation of a material (e.g., a solid material) from a solution of interest (e.g., via precipitation), and perhaps dissolution of that solid material, as part of a processing and/or analysis operation. Advantages of the inventive technology relate to improvements in speed, efficiency, and accuracy, inter alia, relative to known material processing and analysis methods.

Embodiments of the present invention may identify instrumental analyses that could measure the amount of asphaltenes in fossil fuel materials or correlate with coking indexes and perhaps lead to the development of a rapid analysis system.

It is therefore an object of certain embodiments of the present inventive technology to provide a rapid on-column precipitation and dissolution method for rapid measurement of a cyclohexane soluble portion of asphaltenes precipitated from a hydrocarbonaceous solution of interest.

It is an object of certain embodiments of the present inventive technology to provide an automated system for rapid measurement of a cyclohexane soluble portion of asphaltenes.

It is an object of certain embodiments of the present inventive technology to provide an in-vessel precipitation/dissolution system for improved processing (including but not limited to fractionating) of a solution of interest.

It is an object of certain embodiments of the present inventive technology to provide an in-vessel precipitation/dissolution system for improved analysis of a solution of interest (including but not limited to determining the solution's makeup relative to dissolved materials of different polarity).

It is an object of certain embodiments of the present inventive technology to provide an automated analysis and/or processing method using in-vessel material generation.

Naturally, further objects, goals and embodiments of the inventions are disclosed throughout other areas of the specification.

Figure 10:
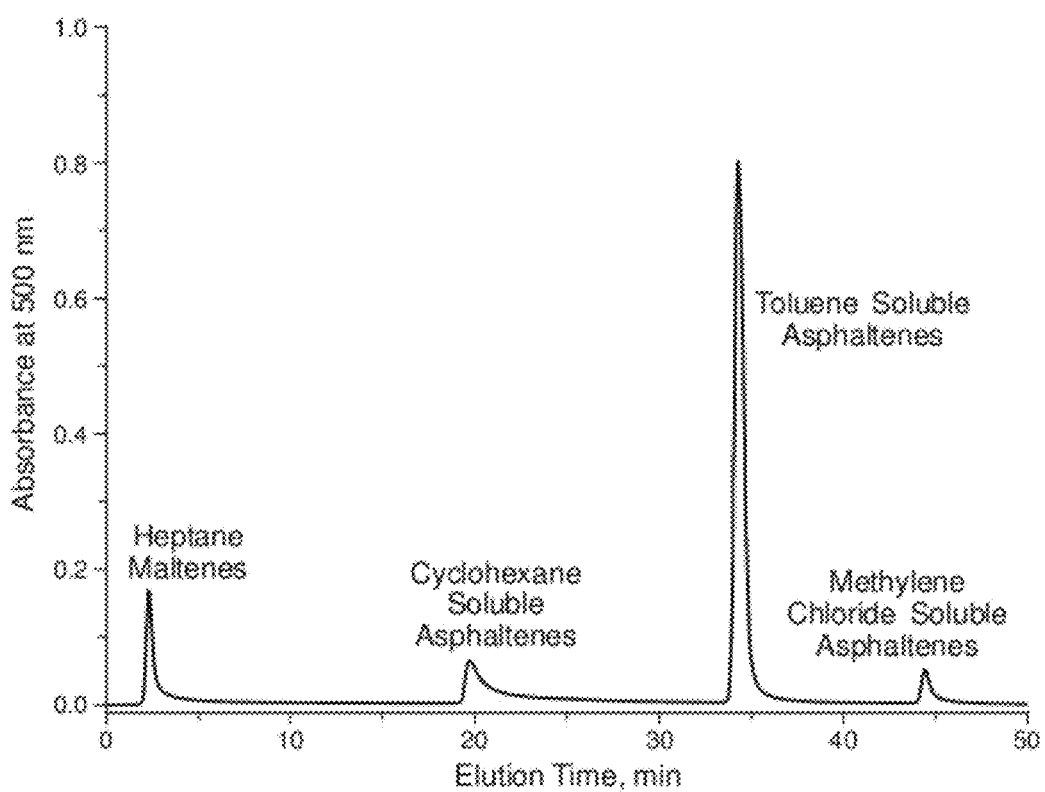

FIG. 10 shows a Separation of 2 mg (10 uL) Unpyrolyzed Boscan Residuum in Methylene Chloride on 250 mm×10 mm PTFE Column, 500 nm Absorbance Detector. Gradient: 0 min. Heptane, 15 min. Cyclohexane, 30 min, Toluene, 40 min. Methylene chloride, 50 min. Heptane, 4.0 mL/min.

Figure 11:
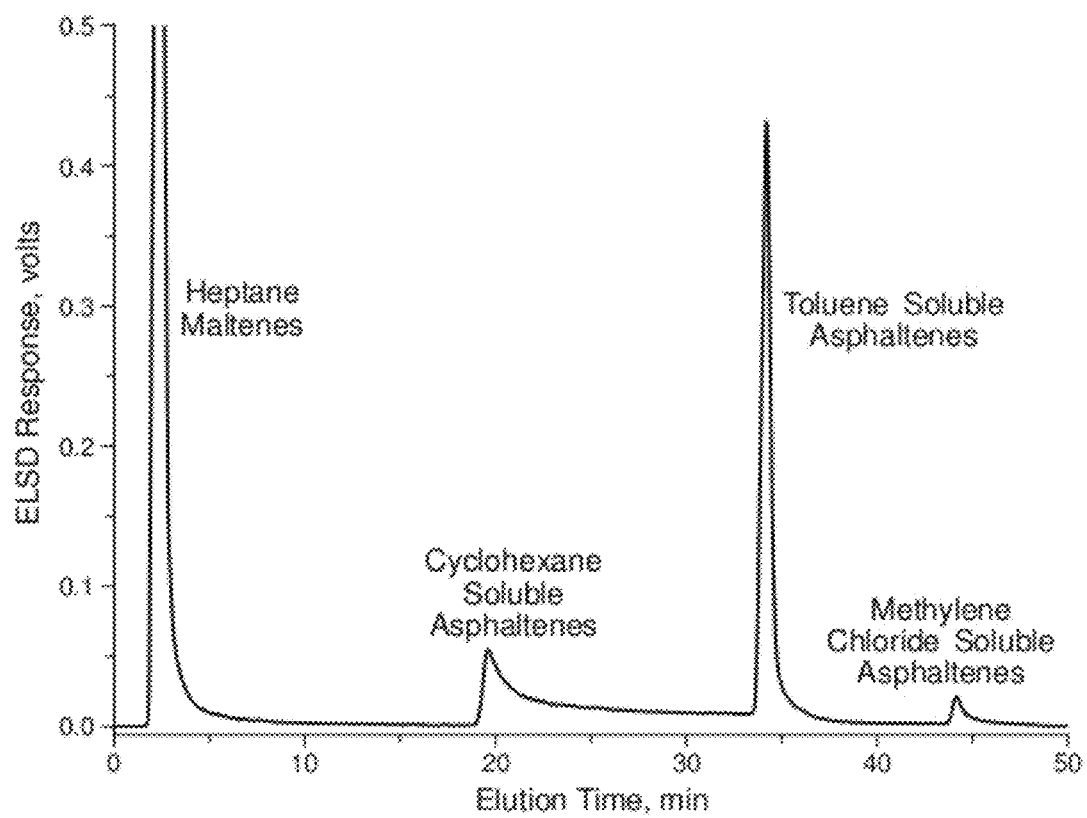

FIG. 11 shows a Separation of 2 mg (10 uL) Unpyrolyzed Boscan Residuum in Methylene Chloride on 250 mm×10 mm PTFE Column, ELSD Detector. Gradient: 0 min. Heptane, 15 min. Cyclohexane, 30 min, Toluene, 40 min. Methylene Chloride, 50 min. Heptane, 4.0 mL/min.

Figure 12:
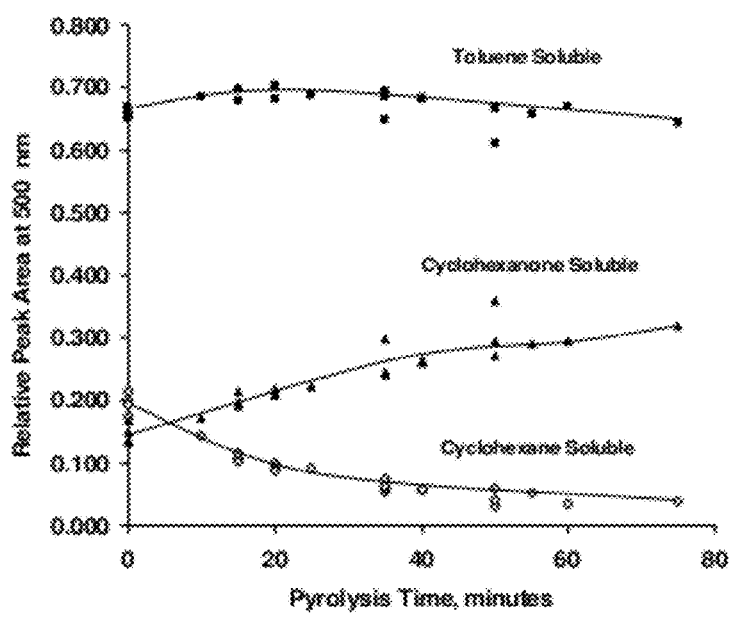
Figure 12:
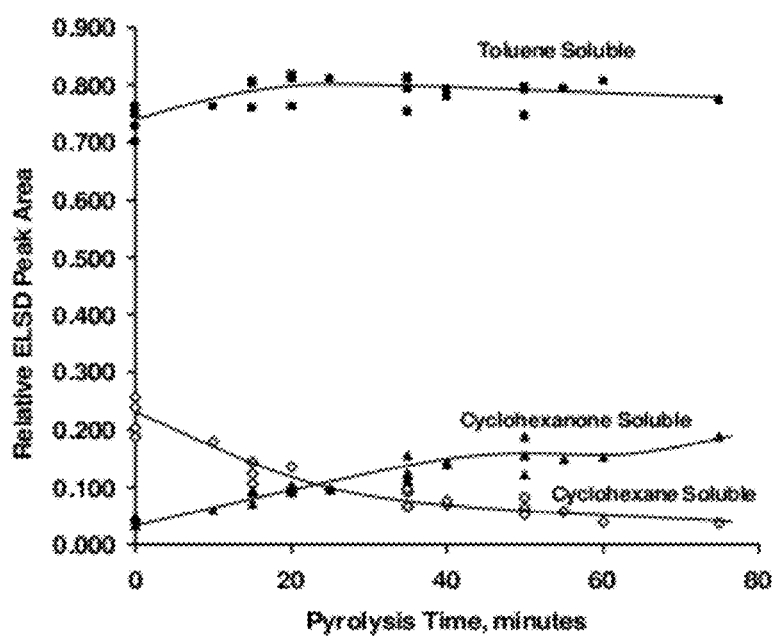

FIG. 12 shows a Relative Peak Areas for Four Original and Pyrolyzed Residua in Cyclohexanone on 250 mm×10 mm PTFE Column, UV 500 nm Detector (top) and ELSD Detector (bottom). Gradient: 0 min. Heptane, 15 min. Cyclohexane, 30 min, Toluene, 40 min. Cyclohexanone, 50 min. Heptane, 4.0 mL/min.

Figure 13:
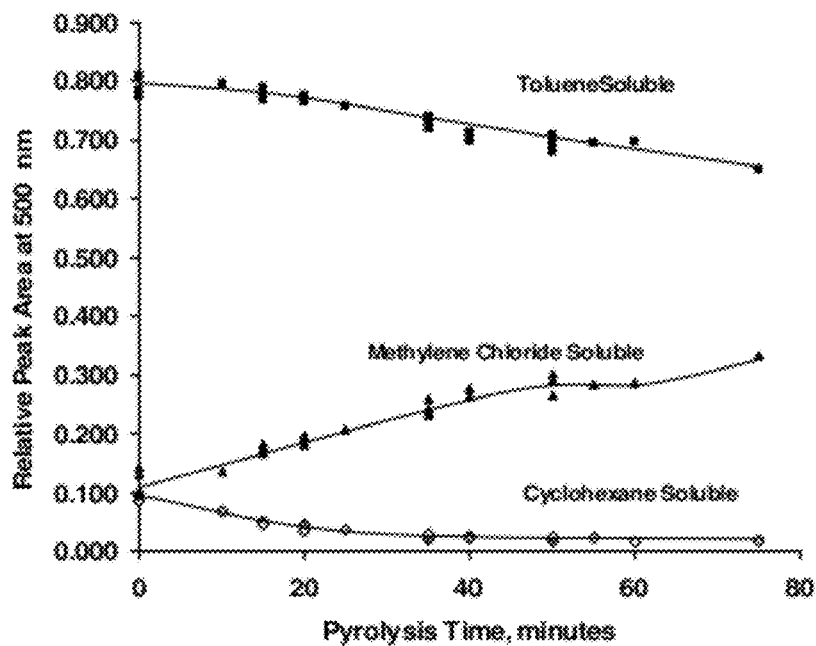
Figure 13:
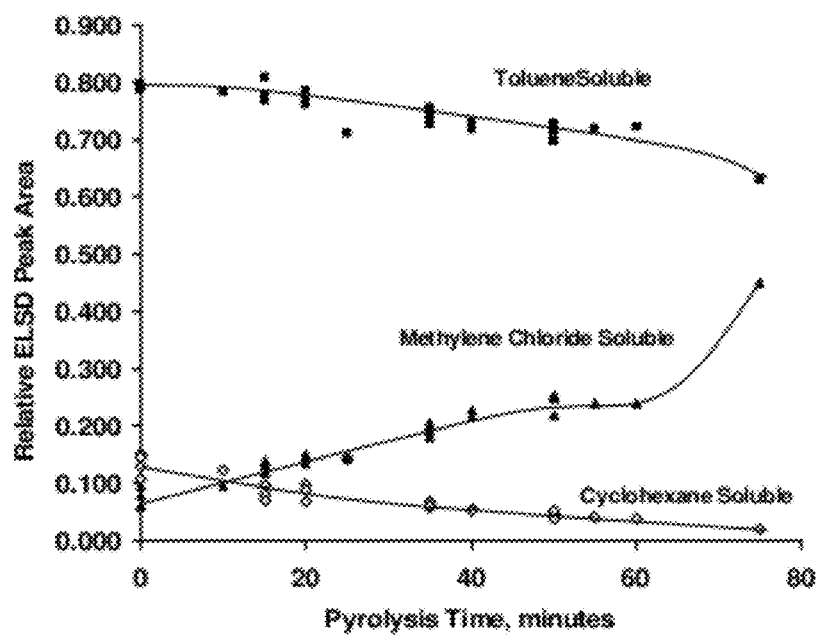

FIG. 13 shows a Relative Peak Areas for Four Original and Pyrolyzed Residua in Methylene Chloride on 250 mm×10 mm PTFE Column, UV 500 nm Detector (top) and ELSD Detector (bottom). Gradient: 0 min. Heptane, 15 min. Cyclohexane, 30 min, Toluene, 40 min. Methylene Chloride, 50 min. Heptane, 4.0 mL/min.

Figure 14:
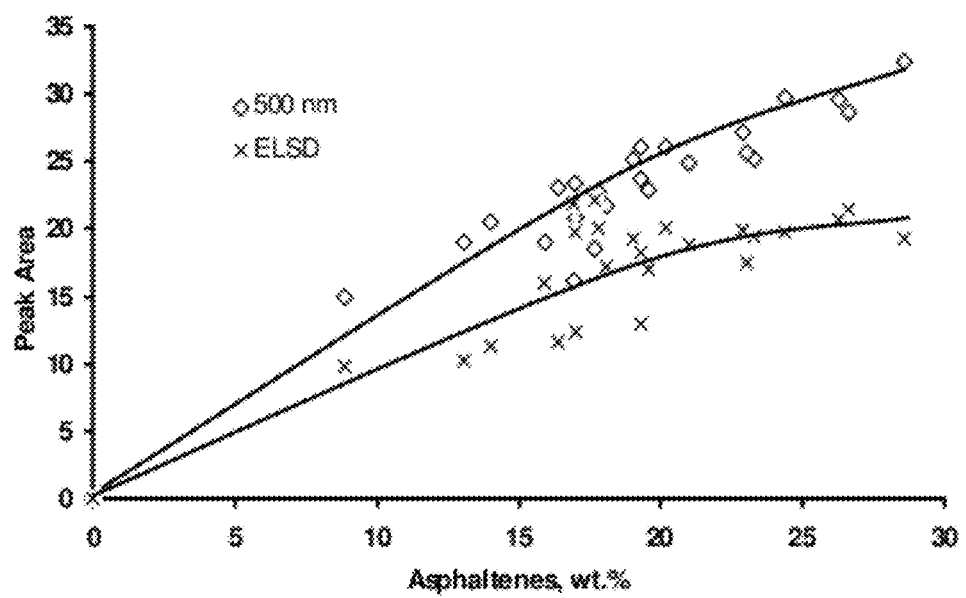

FIG. 14 shows a Correlation of 500 nm Absorbance Detector and ELSD Peak Areas for Four Solvent Separation with Cyclohexanone with Values from Gravimetric Determination of Heptane Asphaltenes.

Figure 15:
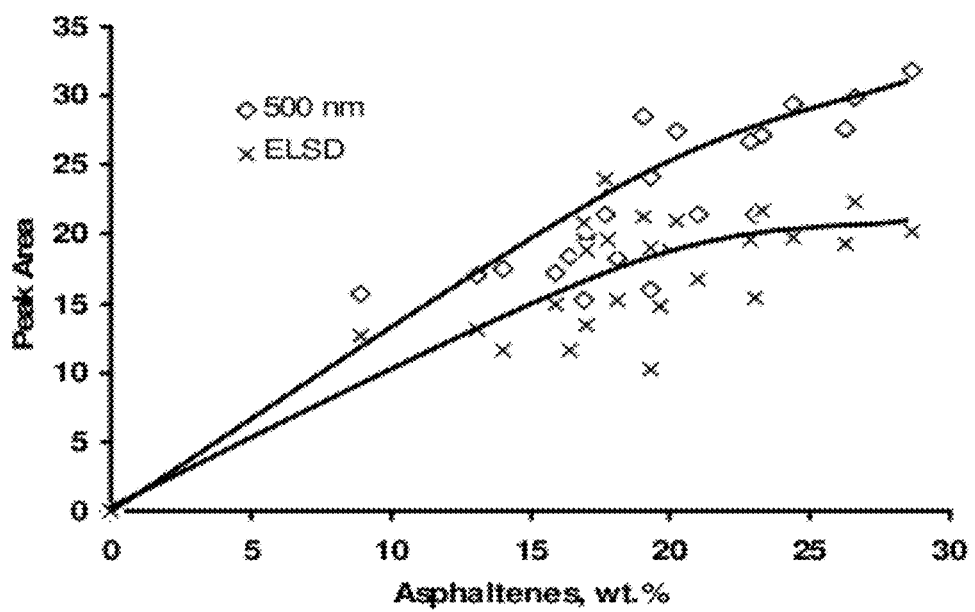

FIG. 15 shows a Correlation of 500 nm Absorbance Detector and ELSD Peak Areas for Four Solvent Separation with Methylene Chloride with Values from Gravimetric Determination of Heptane Asphaltenes.

Figure 16:
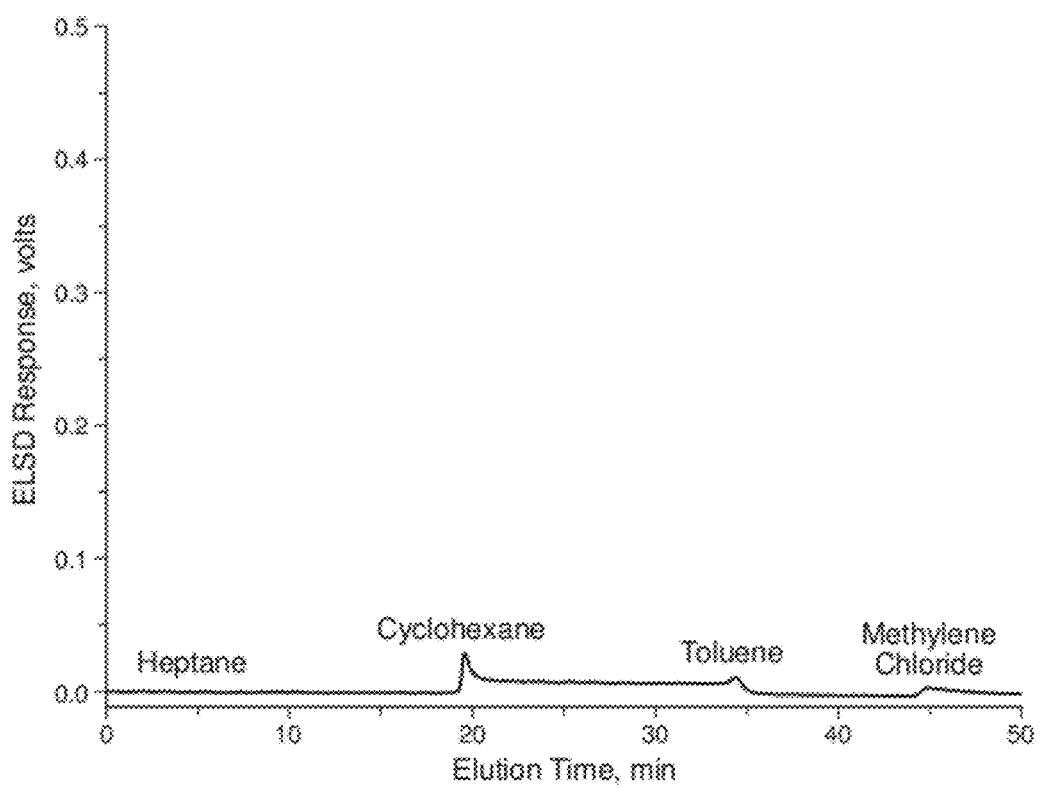
Figure 17:
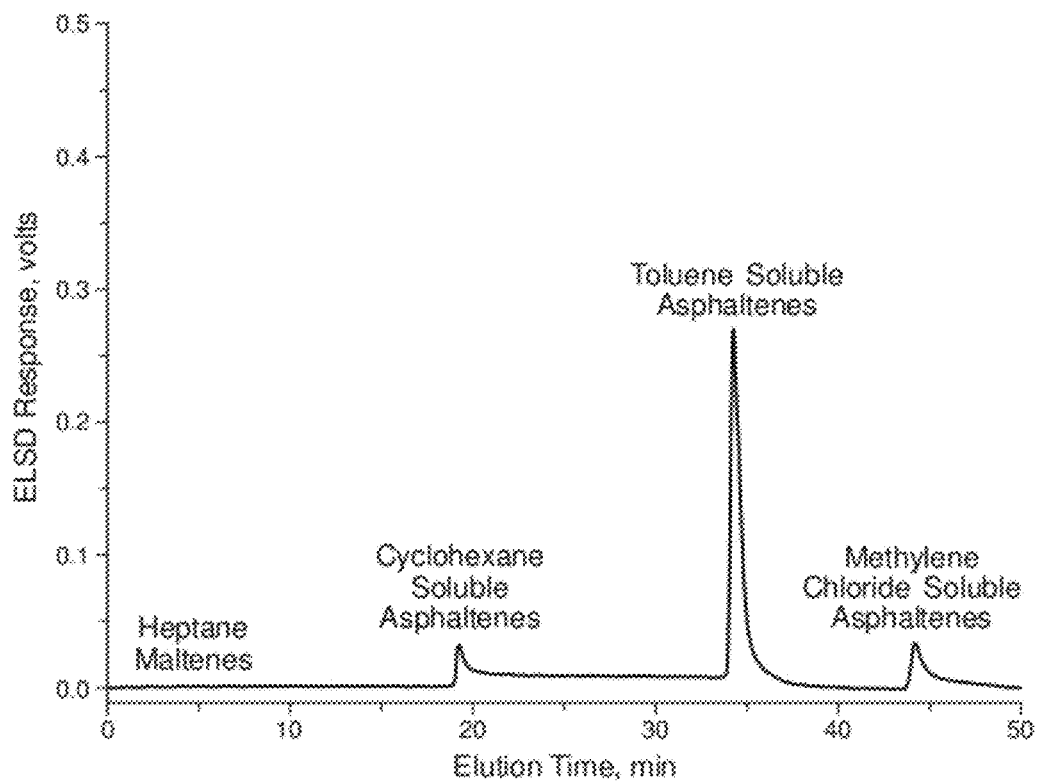
Figure 18:
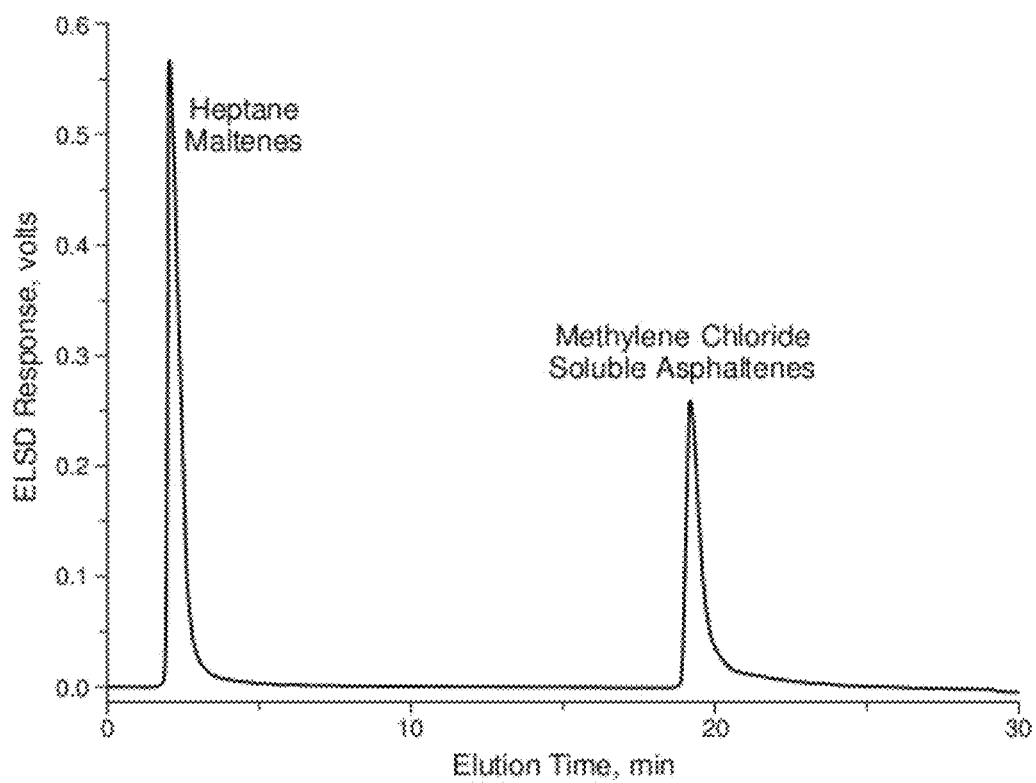

FIG. 16 shows a ELSD Separation Profile for 10 cc Methylene Chloride Blank Injection FIG. 17 shows a ELSD Separation Profile for 0.38 mg Boscan Heptane Asphaltenes in 10 uL Methylene Chloride FIG. 18 shows a ELSD Separation Profile for 0.50 mg Unpyrolyzed Boscan Residuum Boscan in 10 uL Methylene Chloride.

Figure 19:
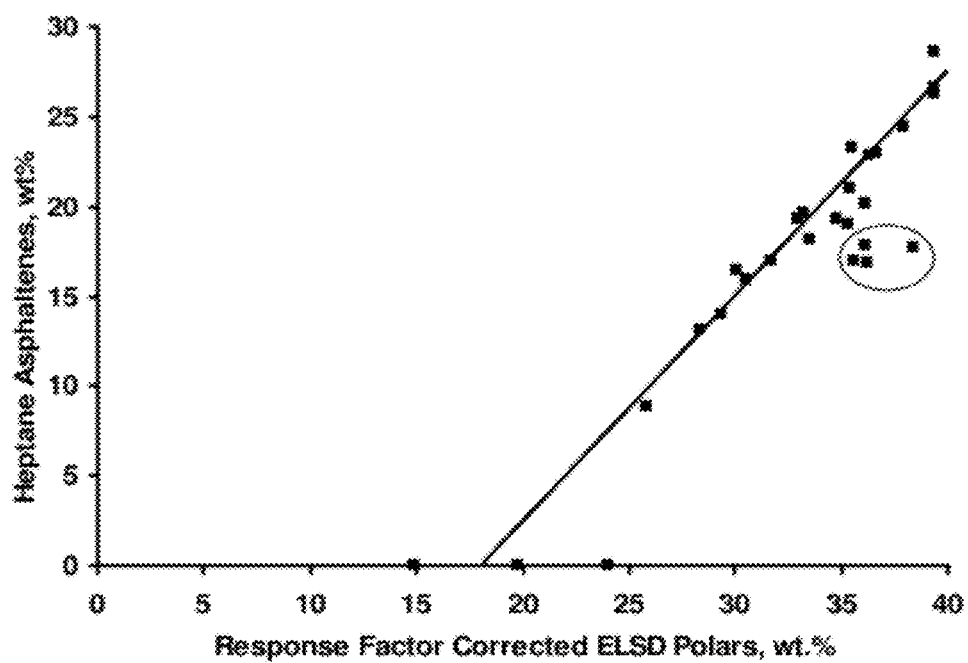

FIG. 19 shows a Correlation Between Weight Percent Gravimetric Asphaltenes and Weight Percent ELSD Polars from Two-Solvent Separation.

Figure 20:
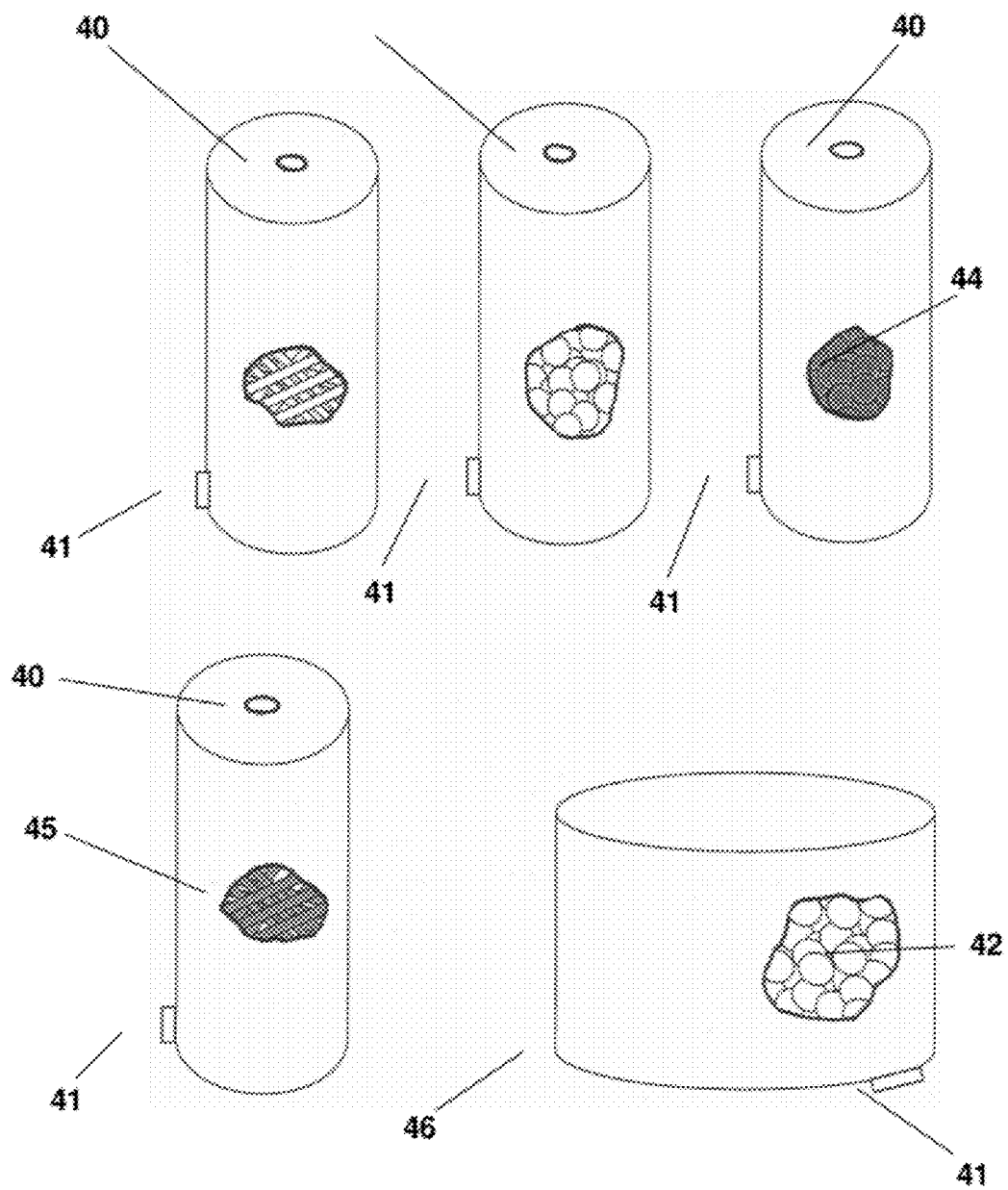

FIG. 20 show vessels as may be used in certain embodiments of the inventive technology, with sectional cutouts affording a view of packing material, and material precipitated thereon.

Figure 21:
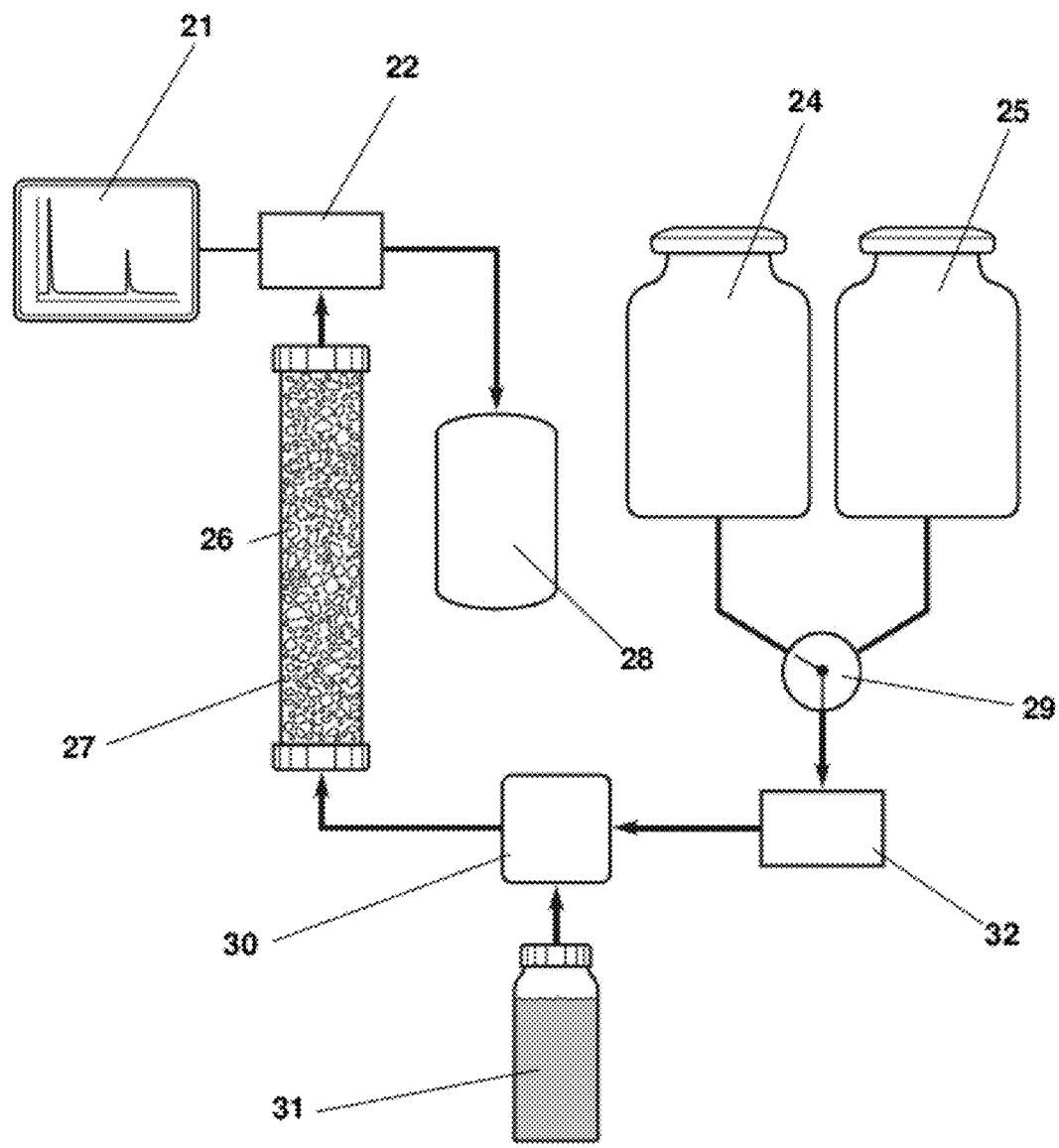

FIG. 21 shows a schematic of components of an apparatus, including chromatographic equipment, that may be used in certain embodiments of the inventive technology.

Figure 22:
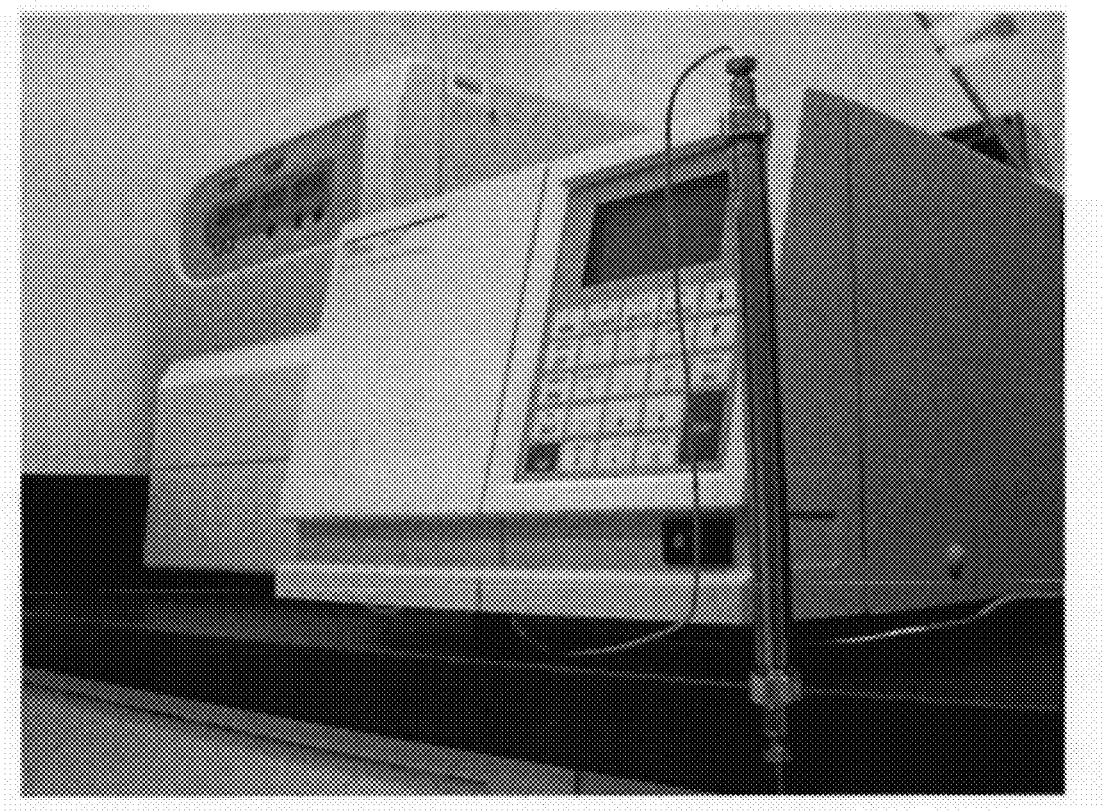

FIG. 22 shows a PTFE-packed stainless steel column in accordance with certain embodiments of the present invention.

DESCRIPTION OF THE PREFERRED EMBODIMENTS

As mentioned earlier, the present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

At least one embodiment of the inventive technology may be a method that comprises the steps of establishing a precipitant in a vessel (a column 27 or a batch type vat 46, as but two examples) having a stationary phase (lattice type or packing material 26, as but two examples) established therein; adding a solution of interest 31 (e.g., oil, or any other material which one desires to process or analyze in any fashion) to the vessel; precipitating a material (e.g., a solid material, a viscous liquid material, and/or a gel material) from the solution of interest; and generating a remnant liquid upon performing the step of precipitating a material from the solution of interest. The step of establishing a precipitant (any material that effects precipitation) in a vessel may be performed by adding the precipitant (heptane, pentane, and/or isooctane, as but a few examples) to the vessel in liquid form, but indeed other methods (e.g., adding a powder form of the precipitant to the vessel and then adding a dissolving liquid) may be used. It is of note that any vessel used for large scale processing (as opposed to analysis of a small sample such as an aliquot), is referred to as a batch type vessel.

The vessel may be a column or batch type vat (as but two examples). Typically, but not necessarily, a column would be used when the method were employed for solution analysis (measuring asphaltene content of an oil or estimating an onset of coking that might occur during processing of oil, as but two of many examples), and the batch type vat would be used when processing a solution (fractionating oil, as but one of many examples). The stationary phase (whether lattice, packing material, or other) may be substantially inert in that, e.g., it is designed such that there is no or minimal interaction, such as absorbance, of the stationary phase with the contacting solution or solute, in some embodiments. Such a substantially inert stationary phase includes but is not limited to oligomers or polymers of polytetrafluorethylene, also known as PTFE (Teflon), polyphenylene sulfide, silicon polymer, fluorinated polymers or elastomers (e.g., Vitons), or PEEK stationary phase. However, in some embodiments, it may be desired that the stationary phase (whether lattice, packing material, or other) is not substantially inert (i.e., it is chemically interactive), and that indeed it is selected such that there is some interaction between it and the contacting liquid (whether solvent, solute, solution or other). It is also of note that any of such stationary phases, whether packing material or lattice, or other, need not be solid (e.g., need not be solid PTFE, e.g.), but instead can indeed be only coated with the indicated material. Packing material can be beaded, ground, chipped, small rods, pebbled, or blocked, as but a few examples—essentially of any form that can be packed in a column.

One fact pointing to the non-obviousness of certain embodiments of the inventive technology is the precipitation of material on or within a substantially inert stationary phase, as columnar liquid chromatography requires adsorption effects (i.e., "non-inertness", or chemical interaction) between the stationary phase and passing substrates dissolved in solution for operation. It is also of note that for a stationary phase to be established in a vessel, it certainly need not, but may, fill most of or all of the entire volume of the vessel.

The solution of interest added to the vessel in certain embodiments of the inventive technology may be oil or any other material which one desires to process and/or analyze in any fashion (wine, water, biological fluids, as but a few examples). Indeed, one may desire to determine information that relates more specifically to the asphaltenes in oil, tannins in wine, metals (or other impurities) in water, and proteins in biological fluids, as but a few examples. The precipitated material may be in (not presented mutually exclusively) powdered form, granular form, layered form, coated form, and/or lump form, as but a few examples; it may be solid, gel, and/or viscous liquid. Basically, certain dissolved solution constituent(s) may come out of solution upon the solution's contact with the precipitant. Often, what is seen is solid material that coats the stationary phase, or portions thereof (e.g., it may precipitate within the packing bed). Of course, by material generation is not meant the creation of new mass from nothing, but rather a generation of a gel, viscous liquid, and/or solid material that was not present before in such gel, viscous liquid, and/or solid form. It is of note that indeed, a gel and even a viscous liquid may include solid material.

Typically, the precipitant will have a polarity that is sufficiently different from the solution of interest so as to effect precipitation of a material from the solution of interest. It is of note that the precipitant may also be referred to as a precipitant solvent in that there typically will be a remnant liquid (e.g., a remnant solution) generated during the precipitation event; the term precipitant solvent may be appropriate in such instances because upon interaction of the precipitant with the solution of interest, some material (e.g., precipitant insoluble material) may be precipitated from the solution while other material (e.g., precipitant soluble material) may remain dissolved in what, after the precipitation, may be referred to as remnant solution. In a situation where all of the dissolved material in the solution of interest is precipitated, then what remains is a remnant liquid, not a remnant solution.

At least one embodiment of the inventive technology may comprise a method comprising the steps of: establishing a precipitant in a column of a liquid chromatograph apparatus (equipment typically used for liquid chromatography); adding a solution of interest to the column; intentionally precipitating a material in said column to yield a remnant liquid; and determining at least one characteristic of said solution of interest. Indeed, as those of ordinary skill in the art would appreciate, the step of intentionally precipitating a material (e.g., solid, gel, and/or viscous liquid) in a liquid chromatograph column is entirely unconventional and counter chromatographic procedure in that standard liquid chromatographic protocol requires a mobile phase in which an added solution is entirely soluble; of course, the step of intentionally precipitating is performed wherever the precipitation is non-accidental (e.g., whenever it occurs as a result of an appropriate selection of material as a precipitant). Typically, in order to precipitate, as is well known, polarities or other chemical characteristics (acid/base interactions, chelation, chemical reaction, protein binding, etc.) of the precipitant and the solution out of which a material is to be precipitated need to be sufficiently different. Embodiments covered by these methods include primarily analysis of the solution of interest. Indeed, the step of determining at least one characteristic of a solution is performed whenever any sort of analysis occurs (whether that analysis be of a dissolved material solution, of a precipitated material, a remnant solution, or other substance).

Examples of determining at least one characteristic include but are not limited to the following: determining a coking index, and determining a solution constituent amount (e.g., determining an amount of heptane asphaltenes that are soluble in cyclohexane soluble or other solvents, determining a height or area of a peak of a separation profile, determining a fractional amount of precipitated material, determining a polarity-based makeup of a solution). Such characteristics may be useful in control of one or more of the following: oil processing, oil fractionating, oil production processes, pipeline fouling, hydrotreating, distillation, vacuum distillation, atmospheric distillation, visbreaking, blending, asphalt formation, extraction, coking onset estimation and fouling, as but a few examples. It is of note that although an important application of embodiments of the inventive technology may be processes or analyses involving hydrocarbonaceous materials (e.g., oil, in any of its many forms, such as but not limited to crude oil), other materials may also be the "solution of interest" in inventive methods described herein. It is also of note that at times, it may be desired to determine a characteristic about a material that is not in solution. In such cases, it may be necessary to first convert such material into solution form (e.g., by adding a solvent thereto) so that processing and/or analysis using the inventive methods described herein may be employed. Further of note is the fact that the term solvent is a broad term that includes "pure solvents" (e.g., straight methylene chloride), in addition to solvent mixtures.

As mentioned, certain embodiments may focus on processing of the solution of interest. Such processing may include, but is not limited to: fractionating the solution of interest (fractionating oil, as but one example), removing unwanted materials from the solution of interest, purification of the solution of interest, extraction of a constituent of the solution of interest, and preparing the solution of interest for further processing. Indeed, the solution of interest may be generated upon adding a solvent to a material which one desires to process and/or analyze. When such preparation is called for, the solution of interest is still processed and/or analyzed, even though the information gleaned therefrom must perhaps thereafter be further manipulated to yield information about the material itself (as opposed to the solution of interest).

At least one embodiment of the inventive technology may be an apparatus that comprises a vessel adapted to allow passage of one or more substrates (e.g., any substances, including chemical solutions such as, but not limited to, oil) through at least a portion of the vessel; a stationary phase either established in the vessel or configured for establishment in the vessel; an inlet 40 to the vessel (through which any of precipitant, solution of interest, and/or solvent may be added); and an outlet 41 from the vessel (through which any liquid (e.g., dissolved material solution) may be removed from the vessel), where the stationary phase is substantially chemically inert relative to all of the one or more substrates that pass through at least a portion of the vessel and contact at least some of the stationary phase. The inlet and outlet, particularly where it's an analytical system that is not purely gravity flow (e.g., where it uses high performance chromatography equipment) may be anywhere on the vessel; perhaps, particularly in non-continuous flow systems, they are one in the same and controlled by a valve(s). A stationary phase is established in the vessel when it is situated in the vessel in any manner; for example, packing material 42 may be packed in the vessel and/or a lattice 43 may be situated in the vessel, in some manner.

A stationary phase is configured for establishment in the vessel when, e.g., it is not provided in the vessel, but instead is in any form that enables it to be established in the vessel. For example, packing material is typically readily establishable in a vessel, as it may be simply placed (e.g., poured) into the vessel, and perhaps also packed down. A lattice type stationary phase is configured for establishment in the vessel when it can be, perhaps after some re-configuration by an operator, placed in the vessel. It is of note that an inlet to the vessel may be quite large in certain circumstances (e.g., an "open" upper end that a batch type vat may have); of course, it may also be smaller (e.g. particularly as it may be in the case of a column). The outlet may be simply a passage through which material may be removed from the vessel, whether permanently open or openable/closeable. Particularly in a batch type system, the outlet may be an openable/closeable drain (e.g., a stopcock).

Also worthy of mention is that in certain columnar embodiments of the inventive technology, the column need not be vertical. Indeed, the column may be established to have any spatial orientation (vertical, horizontal, tilted, etc.) Gravity flow columnar embodiments may involve "off-horizontal" oriented columns; typically, a gravity flow column would be vertically situated. However, many embodiments, particularly those using high performance chromatography equipment (where the column is internally pressurized in significant manner), may involve a column (or other vessel) exhibiting any orientation. It is also of note that in particular embodiments, certain columns may be adapted for use with chromatography equipment. Simply, as such, they may be used as part of a chromatograph apparatus.

The stationary phase, whether lattice, packing material, or other, may, in some embodiments, be substantially inert (e.g., chemically inert) relative to all of the one or more substrates (substances) that pass through at least a portion of the vessel and contact at least some of the stationary phase. Such an inert stationary phase may improve analysis and processing in that the precipitate (at least a portion of which typically precipitates directly onto the stationary phase) does not then chemically interact as is observed with a "non-inert" stationary phase. It is important to understand that the term inert, at the least, includes inert relative to those substrates that the stationary phase will contact. As such, for example, a material that is chemically interactive with only a small group of compounds (i.e., not inert relative to such compounds) is still considered inert relative to this inventive technology if such small group of compounds is not to contact the stationary phase. It is also of note that the term inert, or substantially inert (as opposed to the term completely inert) allows for a small, minimal degree of interaction between the stationary phase and any of the substrates that contact it, as complete inertness is difficult, if not impossible to achieve in some cases. Substantially inert may include causing reactions that impair results—whether analytical or processing—to an acceptable degree. Glass bead packing material, for example, may not be considered a substantially inert stationary phase. In some applications (e.g., some biological assay related applications), an inert packing material may not be desirable, and a packing material that interacts with one or more constituents may be desirable.

At least one embodiment of the inventive technology may be a method that comprises the steps of: adding a solution of interest to a vessel having stationary phase established therein; generating a solid material in said vessel and from the solution of interest; generating a remnant substance upon performing the step of generating a solid material; establishing a solvent in the vessel so that it contacts the solid material; and dissolving at least a portion of the solid material to generate a dissolved material solution. The step of generating a solid material in the vessel and from the solution of interest includes, but is not necessarily limited to, precipitating a solid material from the solution of interest (e.g., precipitating an asphaltene). It is also of note that the remnant substance, in the case of precipitation, is a remnant liquid. Establishing a solvent in the vessel (e.g., adding a solvent to the vessel) so that it contacts the solid material will, of course, dissolve at least a portion of the solid material, if the solvent added does indeed have a greater power to dissolve the solid material than does the precipitant that effected, at least in part, its generation. It is of note that even though what may coat a stationary phase appears strictly gelatinous, indeed solid material makes up at least part of the gel appearing material.

Given the general rule that like dissolves like (i.e., a substance of a first polarity will dissolve a substance of a second polarity where their polarities are sufficiently similar), if the precipitated material is of high polarity (e.g., asphaltenes of oil), then the solvent(s) should be of higher polarity than the precipitant. If successive treatments with different solvents are to be added to the vessel to determine which amounts are soluble in that solvent, then later added solvents should have a polarity that is closer to that of the precipitated material than earlier added solvents. Such is the reasoning behind one (of many) successive asphaltene dissolution protocol—heptane is first used as the precipitant, then the solvent cyclohexane is used, then toluene is used, and then methylene chloride is used (perhaps to dissolve all remaining precipitated material). In such protocol, each successive solvent is of higher polarity. It is also of note that the precipitant may be chosen such that it has a polarity that is less than some constituent(s) of the solution of interest, while at the same time greater than other constituent(s) of the solution of interest.

Successive dissolution protocols may involve the step of successively dissolving at least one additional portion (e.g., in addition to that dissolved by the first non-precipitating solvent) of the generated material with at least one additional solvent to generate at least one additional dissolved material solution. Of course, as mentioned, it is typically necessary to separate the existing dissolved material solution from a space contacting the generated material so that the subsequent solvent can then dissolve at least an additional portion of the generated material (at some point, a solvent may dissolve all of the remaining generated material). Much information may be gleaned from the solution of interest upon analysis of un-dissolved generated material, or of the additional dissolved material solution.

In certain embodiments of the inventive technology, a solvent may be established in the vessel so that it contacts the generated material (such contact is observed whenever any dissolution occurs). Whenever dissolution of the generated material occurs, a dissolved material solution is generated. Such solution may be analyzed, as mentioned, perhaps with a detector 22, thereby determining a characteristic (by providing any information whatsoever about the solution of interest). Of course, such analysis may be accomplished through the use of any of a number of detectors employing evaporative light scattering, mass spectrometry, conductivity, oxidation/reduction, refractive index, polarimetry, atomic spectroscopy, optical absorbance, x-ray, ultrasound, and/or fluorescence, as but a few of the available techniques. Such detection may occur as the analyzed substance leaves the vessel, while it is in the vessel, or after it leaves the vessel. A typical setup of a detector may be not dissimilar to that found in some liquid chromatography set-ups, where the detector detects liquid as it elutes from the column (in the case of columnar, analytical embodiments), or as it is drained from a batch type vat (e.g., as in the processing embodiment).

Of course, as mentioned, in successive dissolution protocols, it may be desired to add an additional solvent to further characterize (to gather more information about) the solution of interest. Thus, it may be necessary to separate the liquid contacting the generated material (whether that liquid be a remnant liquid or a dissolved material solution) so that the subsequent solvent can be established such that it can further dissolve the generated material. Typically, but not necessarily, such "separating" step includes removing the liquid contacting the generated material from the vessel. Further, "separating" includes "removing", in addition to including "replacing", as where the addition of one liquid into a space occupied by a first liquid forces that first liquid out. Dissolved material solution may be acted upon by a detector 22; removed dissolved material solution 28 may be contained. It is of note that the term material refers not only to the material immediately after precipitation (or other type of material generation), but also to generated material that may remain after dissolution, whether one time or successively.

It is of note that some methods, especially analytical methods, may involve continuous flow systems. As such, at least one liquid may be flowing from the vessel, under pressures that are greater than ambient (e.g., pump pressure effected by pump 32), at any time. Although indeed processing embodiments may involve continuous flow, typically, but not necessarily, a solution processing method, and the batch type vat that may find use in such method, will not be continuously flowing; instead, such processing may involve only gravity flow, and the outlet from the vessel may indeed be closed at least some time during operation. Any type of system may be internally pressurized (especially continuous flow systems); pressures may be any that do not break system components and provide acceptable (e.g., sufficiently accurate when analyzing) results. Internal pressures used in the experimental testing includes 50-500 psi, but highly pressurized systems (e.g., up to 12,000 psi) may also be used. Such systems (or indeed other systems), whether continuous flow or not, may include a solvent selection valve 29.

Those methods, whether analytical or processing, involving successive dissolution, afford considerable opportunity to characterize the solution of interest. Indeed, for certain applications, it may only be necessary to simply generate a material in the vessel (e.g., by precipitation), and then analyze the material and/or the remnant substance (e.g., remnant liquid). But in some applications, more information about the solution of interest may be desired; such additional information may be acquired upon the afore-described successive dissolution protocol. Such additional information, whether stemming from a separation profile 21 (e.g., peak values, such as peak heights, peak sharpness, and peak areas, and ratios thereof; times until, between or during elution(s); absence of peaks; sharpness of peaks, etc.) or from other data, can be, if required, mathematically manipulated (in a manner well known in the art) to provide even more information, thereby enabling even greater control over all types of operations.

Experiments and Results Thereof

Summary

Through a series of experiments, an automated separation technique was developed that provides a new approach to measuring the distribution profiles of the most polar, or asphaltenic components of an oil, using a continuous flow system to precipitate and re-dissolve asphaltenes from the oil. Indeed, at least some of the embodiments of the inventive technology may be automated such that the solution of interest, the precipitant 24, and solvent(s) 25 are added (e.g., injected by injector 30) to the vessel (and perhaps removed therefrom) automatically. Characteristics of the solution of interest may be determined automatically also, perhaps using a detector configured (e.g., programmed) to detect and record during elution or at other appropriate time. Methods of analysis based on this new technique were developed. Many of the techniques used below can be applied to the analysis and/or processing of materials other than oil.

About 37-50% (w/w) of the heptane asphaltenes from unpyrolyzed residua dissolve in cyclohexane. As pyrolysis progresses, this number decreases to below 15% as coke and toluene insoluble pre-coke materials appear. This solubility measurement can be used after coke begins to form, unlike the flocculation titration, which cannot be applied to multi-phase systems. Currently, the procedure for the isolation of heptane asphaltenes and the determination of the amount of asphaltenes soluble in cyclohexane spans three days.

A more rapid method to measure asphaltene solubility was explored using a novel on-column asphaltene precipitation and re-dissolution technique. This was automated using high performance liquid chromatography (HPLC) equipment with a step gradient sequence using the solvents: heptane, cyclohexane, and toluene:methanol (98:2). Results for four series of original and pyrolyzed residua were compared with data from the gravimetric method. The measurement time was reduced from three days to forty minutes. The separation was expanded further with the use of four solvents: heptane, cyclohexane, toluene, and cyclohexanone or methylene chloride. This provides a fourth peak which represents the most polar components, in the oil. A method which uses a two solvent step gradient: heptane and methylene chloride, was explored also. A calculation based on the percent area of the second peak relative to the total area of both peaks correlates well with gravimetric asphaltene content. Gravimetric heptane asphaltenes typically can be isolated from an oil only after the polar material represented by the second peak exceeds a minimum threshold value in the oil sample. Methods based on the new on-column precipitation and re-dissolution technique provide significantly more detail about the polar constituents of an oil than does the determination of gravimetric asphaltenes.

In particular embodiments, the present invention may provide exploration of rapid measurements of asphaltene solubility perhaps using an on-column material precipitation and dissolution technique. Measurements may be automated perhaps using liquid chromatography equipment (e.g., high performance liquid chromatography ("HPLC") equipment), perhaps with a step gradient sequence using solvents of increasing solvent strength such as but not limited to heptane, cyclohexane, toluene:methanol mixtures and the like. Results using a column packed with ground PTFE stationary phase for an original and pyrolyzed residuum may correlate well with data from a gravimetric method, and a measurement time may be reduced from about three days to perhaps less than three days such as but not limited to about thirty minutes. As adsorption effects may be observed with non-inert stationary phase, some embodiments focus on the use of substantially inert stationary phase; however, the inventive technology is not limited to methods using only substantially inert stationary phase. In certain embodiments, a stainless steel column packed with ground PTFE may be used to provide a substantially inert matrix perhaps with minimal adsorption characteristics for a separation to determine an amount of heptane asphaltenes and an amount of the asphaltenes that dissolve in cyclohexane. Methods can, inter alia, be used to provide a rapid direct measurement of the heptane asphaltenes content of oil, asphalt or the like. The inventive techniques also offers the possibility of developing preparative or process level separations of petroleum materials to remove polar materials to generate an improved quality feed for subsequent processing. Of course, the experiments and the results presented herein are in no way intended to limit the scope of the inventive technology.

Experimental Background

Petroleum residua consist of a continuum of associated polar asphaltene complexes dispersed in a lower polarity solvent phase by intermediate polarity resins. When the residuum is heated to temperatures above 340 deg C. (650 deg F.), the ordered structure is systematically and irreversibly destroyed, leading to coke formation following an induction period. An important consideration in the refining industry is to be able to measure how close a pyrolyzed material is to forming coke on the coke induction period timeline. Undesired coking during distillation results in significant down time and economic loss. To avoid this problem, conservative heating profiles are often used, which results in less than optimal distillate yield, and less profitability. The proximity to coke formation can be measured using the WRI Coking Indexes, which are calculations based on flocculation titration data or the solubility of heptane asphaltenes in cyclohexane (Schabron et al. 2001a, 2001b). As an example, coking indexes are discussed in U.S. Pat. No. 6,773,921, hereby incorporated herein by reference. The Coking Index values decrease during pyrolysis to a threshold value below which coke formation begins. Currently, the Coking Indexes require lengthy laboratory analysis of a residuum sample. A new, rapid on-column precipitation and re-dissolution method for rapidly measuring the cyclohexane soluble portion of asphaltenes was developed in the current study.

The Solvation Shell Coking Index

Some aspects of the ordered structure of petroleum residua can be modeled by the Pal and Rhodes suspended particle solution model of dispersed solvated particles in a solvent matrix (as discussed in Pal and Rhodes, 1989, *Viscosity/Concentration Relationships of Emulsions*, Journal of Rheology 33 (7) pp. 1021-1045, and Schabron et al. 2001c, each hereby incorporated by reference). The volume fraction of the core of particles can be considered as the volume fraction of heptane asphaltenes $\Phi$. The volume of the core is increased by a solvation shell term $K_S$. Several solvated shells bind a portion of solvent and increase the effective particle volume by a term $K_F$. The term $K_S K_F$ is called the solvation constant K. The effective particle volume $\Phi_{EFF}$ is equal to the core asphaltene fraction volume increased by the solvation terms as shown by the following equation:

$$\Phi_{EFF} = KN_a = K_F K_S N_a$$

The volume fraction of polar asphaltene cores, $\Phi_a$ can be estimated from the mass fraction of heptane asphaltenes $X_a$ divided by an assumed density of 1.2 g/cm$^3$. $K_S$ values for unpyrolyzed residua and asphalt systems are typically near or above 1.6. For pyrolyzed oils the $K_S$ values decrease as pyrolysis progresses and the protective shell surrounding the polar asphaltene core is destroyed (Schabron et al. 2001a). A method for estimating $K_S$ is to measure the mass fraction of heptane asphaltenes that dissolve in cyclohexane (Y) using the equation below.

$$K_S = 1/(1-Y)$$

The above equation assumes that the density of the asphaltenes that dissolve in cyclohexane is essentially the same as the density of the insoluble portion.

Rapid Measurement of Cyclohexane Soluble Asphaltenes: The $K_S$ term is a Coking Index value that we have found to be universally applicable to vacuum or atmospheric residua or whole visbroken oils. To obtain this value the amount of heptane asphaltenes that dissolve in cyclohexane is measured. For unpyrolyzed residua, about 37-50% (w/w) of heptane asphaltenes dissolve in cyclohexane. This corresponds to $K_S$ values of 1.6-2.0. As pyrolysis progresses, the amount of heptane asphaltenes soluble in cyclohexane decreases below 15% as coke and toluene insoluble pre-coke materials appear, which corresponds to $K_S$ values below 1.2. This is an indicator of the destruction of the intermediate polarity, or resins material. An unstable system results when the depletion of the resins disables the ability of the asphaltene/resin complexes to self-adjust their apparent molecular weights to closely match the solubility parameter of the matrix. At that point on the coke formation induction time line, the ordered system breaks down and the polar asphaltene material is no longer stabilized, and coke begins to form (Schabron et al. 2001a, 2001b).

Residua: The four residua studied were Boscan, Lloydminster, and Redwater, B.C. from prior work at Western Research Institute (WRI), and MaxCL2 provided by ConocoPhillips.

Determination of Asphaltenes: Heptane asphaltenes were isolated by heating an excess (40:1 v:w) mixture of reagent-grade n-heptane and residuum to 70 deg C. (158 deg F.) for about ½ hour on a heated stir plate while stirring with a magnetic stir bar. This was followed by overnight stirring at room temperature. The following morning, the stirring was stopped for 30 minutes prior to vacuum filtration using Ace, 140-mL, 10-20 micron, sintered glass filters. Residual solvent was removed from the asphaltenes on the filters using a vacuum oven set at 120 deg C. (248 deg F.) for 30 minutes. The asphaltenes were cooled in a desiccator prior to weighing.

A portion of n-heptane asphaltenes was ground to a fine powder using a mortar and pestle. A 0.5-g portion of this was weighed into a 120-mL jar, and 100 mL of reagent grade cyclohexane and a magnetic stir bar were added. The mixture was stirred overnight. The mixture was allowed to settle for 30 minutes prior to vacuum filtration using Ace, 140-mL, 10-20 micron, sintered glass filters. Solvent was removed from the filtrate by rotary evaporation, and traces of cyclohexane were removed in a vacuum oven at 100 deg C. (212 deg F.) for 15 minutes. The cyclohexane soluble materials were cooled in a desiccator prior to weighing.

Pyrolysis: Pyrolysis experiments were performed at various residence times with 500-g residua samples in a 4-inch diameter reactor with continuous stirring and distillate removal using a condenser at atmospheric pressure. Residua were evaluated as atmospheric bottoms material without distillate. Coke and pre-coke materials were determined as toluene insolubles (TI) retained on a 10-micron filter.

On-Column Asphaltene Precipitation: The on-column asphaltene precipitation and re-dissolution experiments were conducted using a Waters 717 autosampler, a Waters 60F pump with 600 controller, a Waters 1487 ultraviolet/visible absorbance detector, and an Alltech ELSD 800 detector. Elution solvents were reagent grade, with step gradients between solvents. Solutions of residua and asphaltenes were injected. Peak area integration was performed using a Chrom Perfect Spirit 5.5 data system. Various columns and conditions were tested. Pyrolyzed sample solutions were filtered through a 0.45 micron PTFE filter prior to injection. ELSD separation peak areas were corrected for small blank peaks due to the step gradient solvent changes.

Experimental Results:

A new automated separation technique was developed that provides a new approach to measuring the distribution profiles of the most polar, or asphaltenic components of an oil, using a continuous flow system to precipitate and re-dissolve asphaltenes from the oil.

The Manual Method: To measure the amount of asphaltenes using the manual method, a sample of oil is weighed and mixed with an excess (30:1 ratio or greater, as but one example) of aliphatic hydrocarbon solvent such as heptane. The mixture is stirred overnight, and the asphaltenes precipitate while the maltenes remain in solution. The mixture is then filtered and the precipitate is rinsed repeatedly with the hydrocarbon solvent until the filtrate is clear. The precipitate is then dried thoroughly, usually in a vacuum oven, and weighed. This procedure usually takes about 24 hours. To determine the cyclohexane soluble portion of the asphaltenes, the precipitate is ground manually, and a portion of the ground precipitate is stirred overnight with an excess of cyclohexane. The next day, the mixture is filtered to separate the cyclohexane soluble and insoluble portions. The full manual method to determine asphaltenes and the cyclohexane soluble portion of asphaltenes can take up to 3 days to complete.

The Automated Separation Method: The new on-column separation provides a rapid method using an automated continuous flow system. Bodusynski et al (1982, 1987) reported gravimetric on-column dissolution methods for separating coal liquids and petroleum residua deposited onto various packing materials using sequential dissolution into various solvents. Solutions of sample were directly added to column packing material and the solvent was removed by evaporation outside the column. The packing material coated with sample was then poured into a column. Sequential dissolution with a series of solvents of increasing polarity has also been performed on petroleum residua materials without the use of a column (Schabron et al. 2001b).

The current technique involves on-column precipitation into a low polarity solvent mobile phase combined with subsequent re-dissolution using one or more solvents of increasing solvent strength and polarity. Although high performance liquid chromatography (HPLC) equipment is used, the separation does not involve a chromatographic separation based on adsorption. A weighed portion of oil is dissolved in a solvent of sufficient strength to dissolve the entire sample. An aliquot of the solution is injected onto a column packed with granular (PTFE). In at least one experiment, the initial solvent in the column and the solvent into which the sample solution is injected is heptane. Once the sample solution enters the column with the heptane mobile phase, the heptane displaces and dilutes the injected solvent, and heptane insoluble materials precipitate. The soluble maltenes continue to move with the heptane and they elute from the column. The solvent is then switched to a stronger solvent, or a series of stronger solvents of increasing solvent strength, which dissolves a portion or all of the precipitated material. The solvent is then switched back to heptane in preparation for the next sample injection. Another injection is then made by the autosampler, and the cycle is repeated. Since the elution solvents are being changed, a refractive index detector can not be used. An optical absorbance detector can be used; however, there is some variation in the absorptivities between asphaltenes from different residua, pyrolyzed and unpyrolyzed asphaltenes, and the cyclohexane soluble and insoluble portions of asphaltenes. In the current study, the use of an evaporative light scattering detector (ELSD), which responds more uniformly to a given number of molecules of each of the above materials, was established. The result provides a powerful new automated tool for process control and heavy oil evaluation.

Pyrolysis: Pyrolysis experiments were performed with the four residua to provide additional pyrolyzed atmospheric bottoms samples for different pyrolysis times at 400° C. The amounts of heptane asphaltenes and toluene-insoluble materials in the original and pyrolyzed residua materials are provided in Table 1. Also provided are the calculated $K_S$ values. The $K_S$ values for the four unpyrolyzed residua are all 1.6 or larger, indicating that the residua are far from producing coke on the coke formation induction time line. The data in Table 1 show the characteristic decrease in the $K_S$ Coking Index values as pyrolysis progresses. There are no toluene insoluble materials greater than 10 microns in size in any of the product oils except for the 90-minute Boscan oil and the 75-minute Redwater, B.C. which were pyrolyzed beyond the coke formation threshold.

On-Column Asphaltene Precipitation Optimization Experiments

Experimental conditions were explored to optimize a single set of separation conditions for comparing various original and pyrolyzed residua. The optical absorptivities of heptane asphaltenes, and the cyclohexane soluble and insoluble components of heptane asphaltenes in toluene solution for original and pyrolyzed residua for wavelengths ranging from 400 nm to 700 nm were evaluated. The purpose of these experiments was to determine the wavelength at which the absorptivities showed the least variation between the different materials. Results showed that the shorter wavelength (400 nm) provides more uniform absorptivities than the higher wavelength (700 nm). Wavelengths below 400 nm were not considered due to the strong absorbance of toluene. Although the results indicate that the shorter wavelength of 400 nm should be used, the absorbance for some of the samples was too high at this wavelength for the sample amounts injected in some development work. Therefore, 700 nm was selected for the certain stages of the work. It is important to note in the discussions that follow that only materials that absorb light at 700 nm are being detected. Saturated aliphatic, naphthenic, and aromatic structures that do not exhibit brown color in the visible region are not detected.

Separation Considerations: Over the course of the development work, several important aspects to the separation were better understood. For example, the separation temperature can be near ambient and it does not need to be controlled exactly. In those embodiments where inertness is desired, glass wool or glass beads should not be used since they result in strong adsorption effects. The amount of sample injected should be maximized to minimize adsorption effects, while the amount of solvent injected should be kept at a minimum. Peaks must be resolved well, despite some tailing which is due to continuous re-dissolution of small amounts of material precipitated on the packing. The solvent flow rate must be compatible with the ELSD (in this case <6 mL/min). Since some pyrolyzed samples result in off-scale asphaltene peaks at 400 nm when 2 mg sample portions are injected, a wavelength of 500 nm was selected for the absorbance detector. Blank correction is required for the ELSD peak areas since small, repeatable peaks are observed when the solvents are changed.

Figure 1:
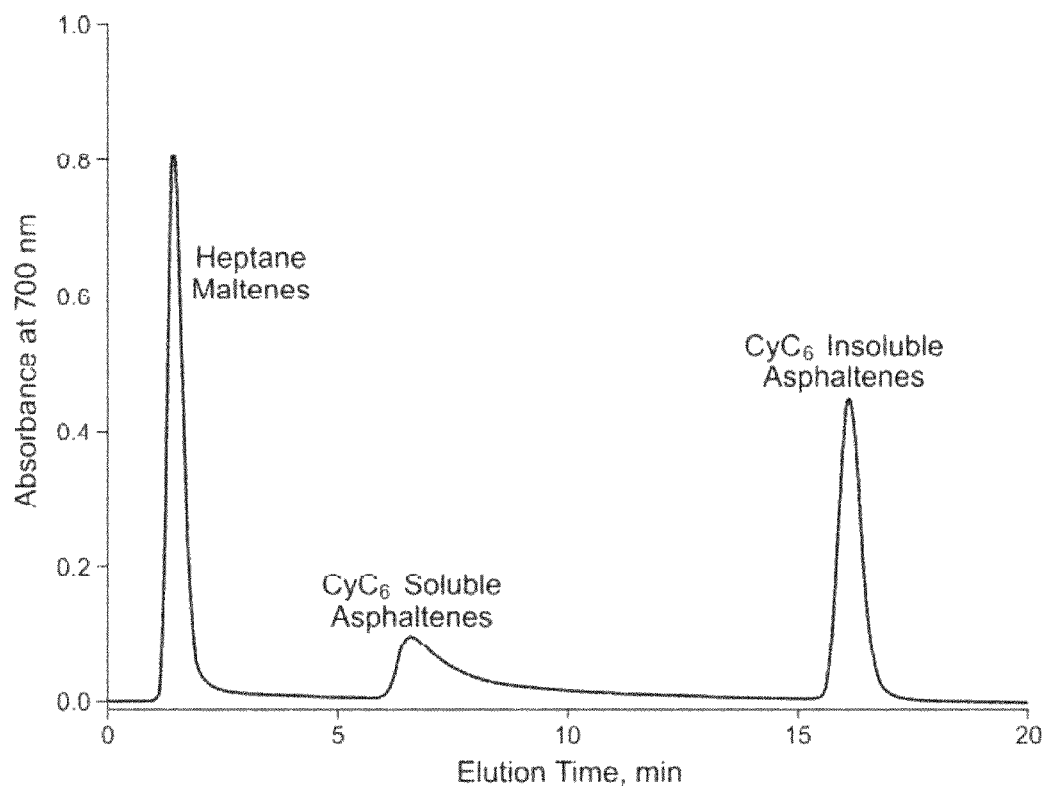
FIG. 1 shows a Separation Profile for 10 mg Redwater, B.C. Residuum on 160×8.0 mm PTFE Column, 700 nm Absorbance Detector. Gradient: 0 min. Heptane, 2 min. Cyclohexane, 15 min. Toluene:methanol (98:2), 40 min. Heptane; 3.0 mL/min.
Figure 2:
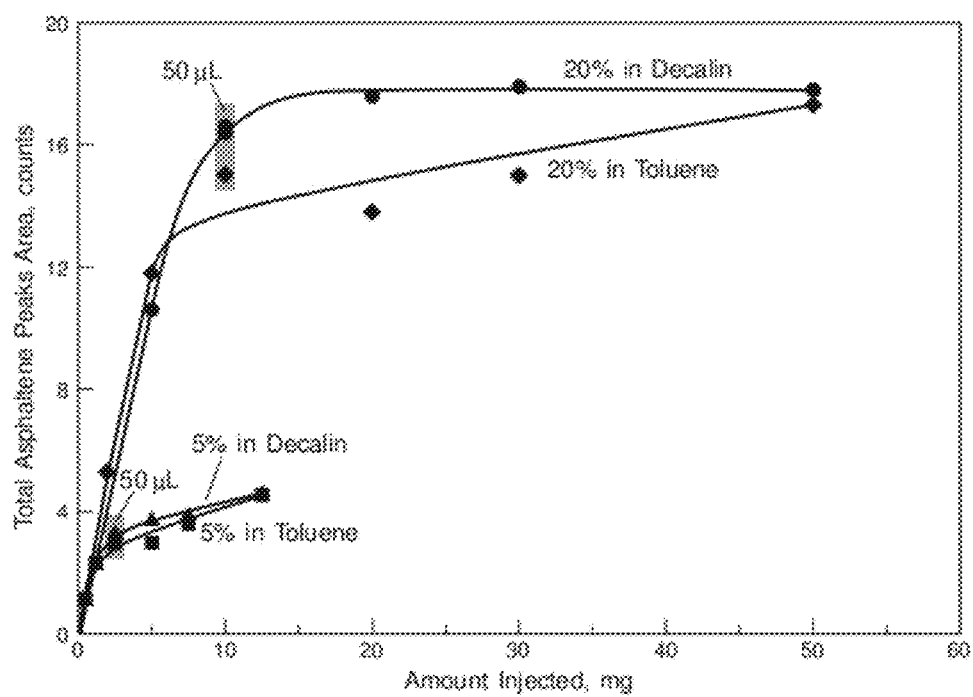
FIG. 2 shows a Sample Size Study with Redwater, B.C. Residuum on a 150 mm×4.6 mm PTFE Column (2.5 cc Volume), 700 nm Absorbance Detector. Gradient: 0 min. Heptane, 1 min. Cyclohexane, 8 min. Toluene:methanol (98:2) (v:v), 14 min. Heptane; 2.0 mL/min.
Figure 3:
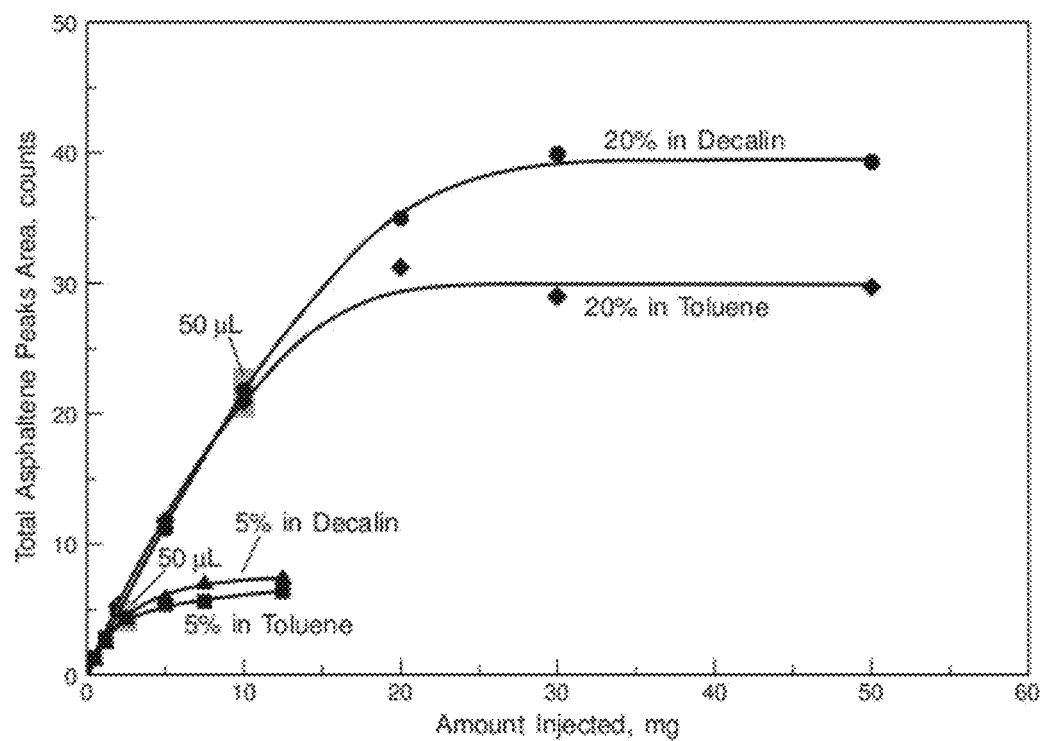
FIG. 3 shows a Sample Size Study with Redwater, B.C. Residuum on a 100 mm×7.0 mm PTFE Column (3.8 cc Volume), 700 nm Absorbance Detector. Gradient: 0 min. Heptane, 1 min. Cyclohexane, 10 min. Toluene:methanol (98:2) (v:v), 15 min. Heptane; 2.5 mL/min.
Figure 4:
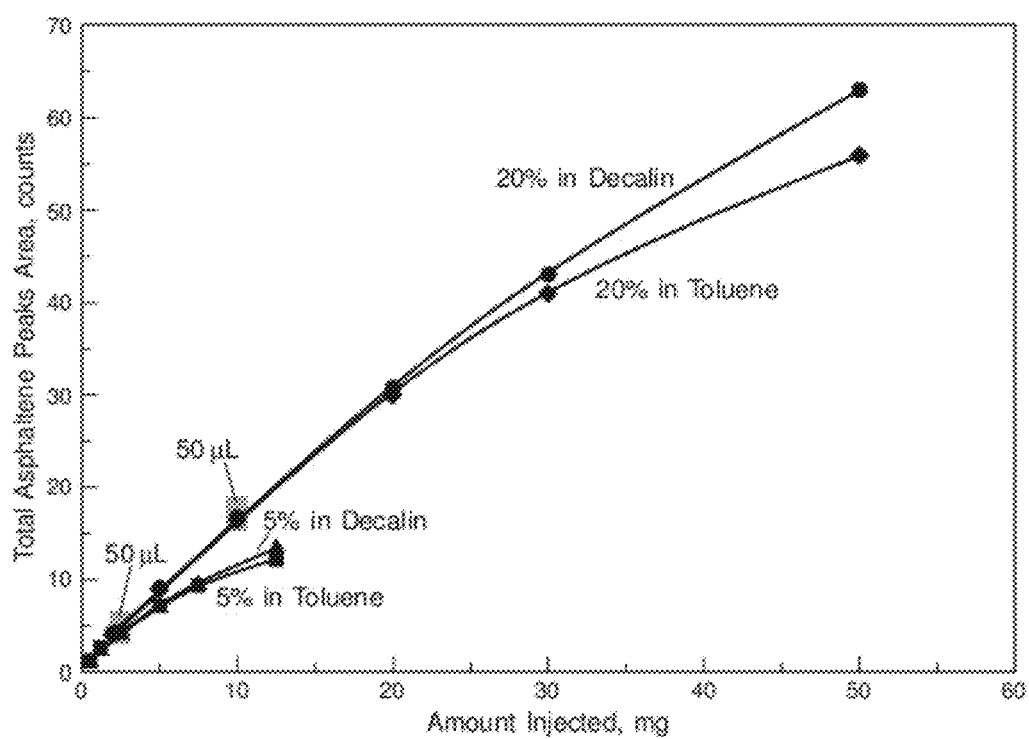
FIG. 4 shows a Sample Size Study with Redwater, B.C. Residuum on a 250 mm×10 mm PTFE Column (20 cc Volume), 700 nm Absorbance Detector. Gradient: 0 min. heptane, 3 min. Cyclohexane, 13 min. Toluene:methanol (98:2) (v:v), 21 min. heptane; 2.5 mL/min.

Sample Amount Injected: The amount of sample injected and the column size to be used are important variables. FIG. 1 shows an initial separation profile at 700 nm for unpyrolyzed Redwater, B.C. residuum obtained early in this study. Although the separation looks good, the resolution between peaks is not optimal. Also, this particular column size is no longer available. A series of systematic experiments was subsequently performed to better understand the effect of column size, volume injected, and sample amount injected. The study also explored any differences that might occur if either toluene or decalin were used as the sample solvent. FIGS. 2-4 show the peak areas for the total asphaltenes (cyclohexane soluble plus cyclohexane insoluble) as a function of amount injected for three different stainless steel column sizes, each packed with 0.25-0.42 mm PTFE stationary phase. The results indicate that the separation conditions are easier to control with the larger column, and that at a low injection volume (<50 uL), toluene can be used as the sample solvent.

This is an important finding since residua samples dissolve in toluene much faster than in decalin.

Three Solvent Separation Conditions: The separation conditions that were established for sample analysis using the initial three solvent system are listed below.

Figure 5:
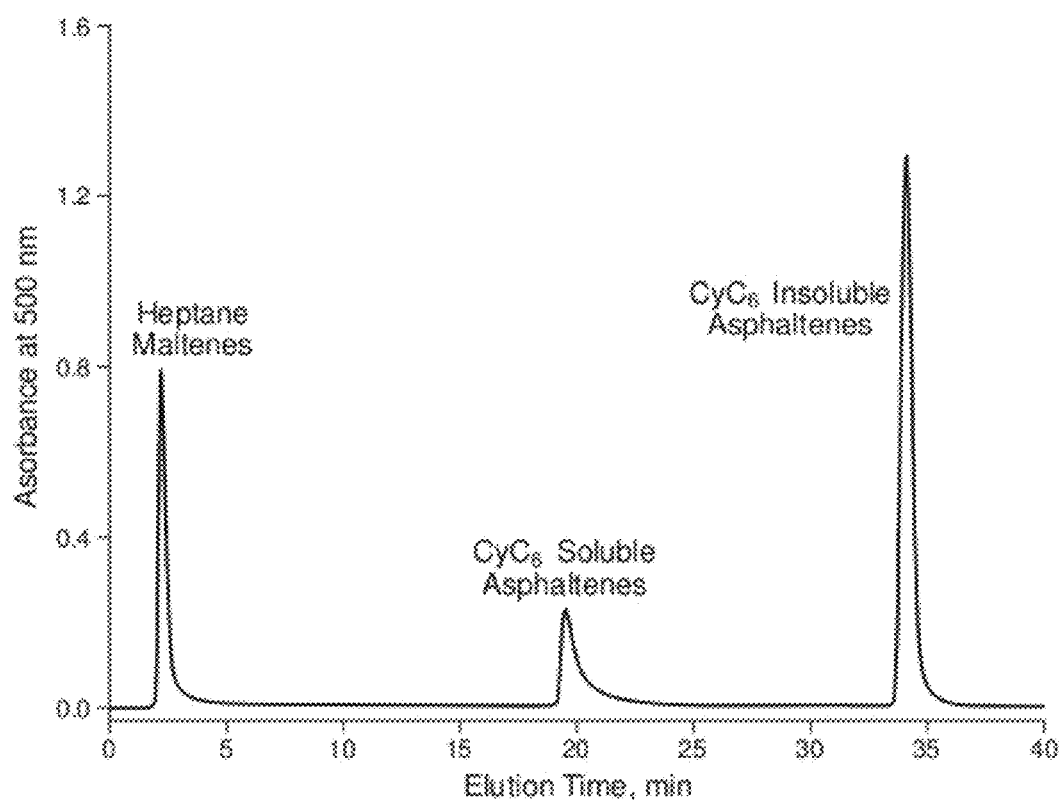
FIG. 5 shows Separation of 2 mg (10 uL) Unpyrolyzed Boscan Residuum in Toluene on 250 mm×10 mm PTFE Column, 500 nm Absorbance Detector. Gradient: 0 min. Heptane, 15 min. Cyclohexane, 30 min, Toluene:methanol (98:2), 40 min. heptane, 4.0 mL/min.
Figure 6:
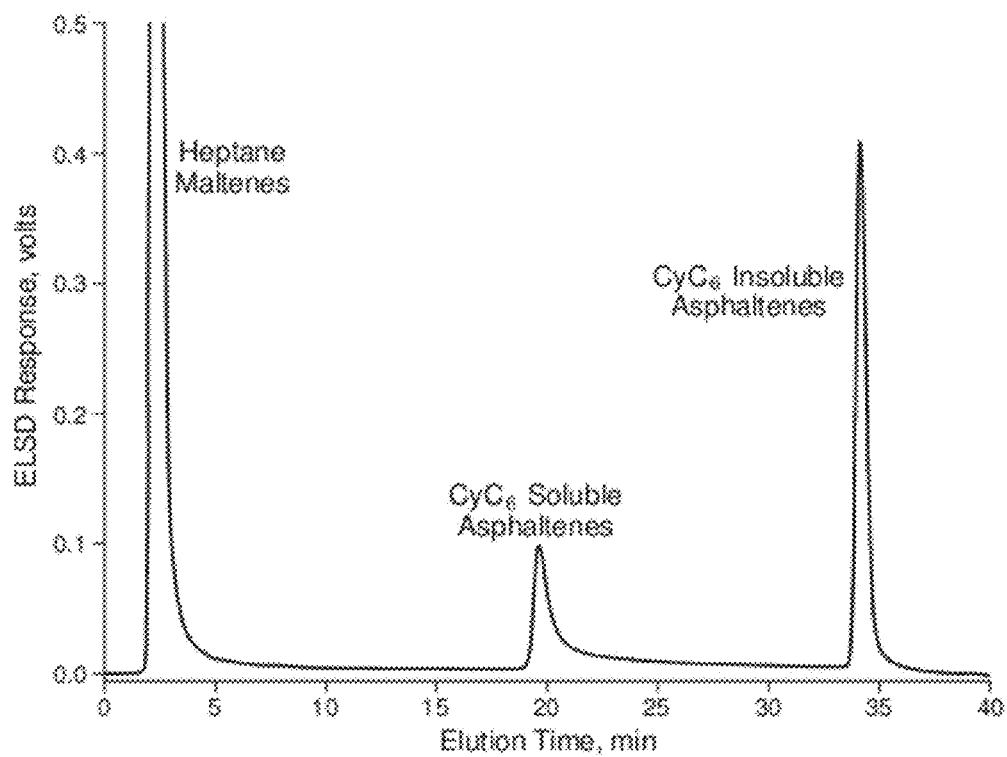
FIG. 6 shows a Separation of 2 mg (10 uL) Unpyrolyzed Boscan Residuum in Toluene on 250 mm×10 mm PTFE Column with ELSD Detector. Gradient: 0 min. Heptane, 15 min. Cyclohexane, 30 min, Toluene:methanol (98:2), 40 min. Heptane, 4.0 mL/min.

1. 250×10 mm stainless steel column (Alltech 96511)
2. 0.25-0.42 mm PTFE stationary phase
3. Solvent flow rate: 4 mL/min
4. Step gradient times: 0 min. heptane, 15 min. cyclohexane, 30 min, toluene:methanol (98:2) (v:v), 40 min. heptane.
5. Sample solutions: 20 wt. % in toluene
6. Amount injected: 10 uL (2 mg)
7. Optical absorbance detector at 500 nm
8. Evaporative light scattering detector (ELSD) at 60° C. and 1.5 bar nitrogen Three Solvent Separation Results: Separation profiles for 10 uL of 20 wt. % unpyrolyzed Boscan residuum in toluene using an absorbance detector at 500 nm and an ELSD are provided in FIGS. 5 and 6, respectively. A comparison of $K_S$ values determined gravimetrically with $K_S$ values determined by the new on-column precipitation and re-dissolution method is provided in Table 2 for a series of original and pyrolyzed residua. Results show that the ELSD data closely track the gravimetric data. $K_S$ values decrease with pyrolysis severity for all four residua. The results for the 500 nm absorbance detector show a similar trend of decreasing $K_S$ values with increasing pyrolysis times; however, the absolute values tend to be somewhat smaller than the corresponding gravimetric or ELSD values. This is due to the relatively lower optical absorptivity at 500 nm for the cyclohexane soluble portion of asphaltenes as compared with the cyclohexane insoluble materials. Both the Boscan 50-minute and the Redwater, B.C. 75-minute pyrolysis product oils contained some insoluble material when the 20 wt. % in toluene solutions were pre-filtered through a 0.45 micron PTFE syringe filter prior to injection. Therefore, it is assumed that not all of the most polar material is being accounted for in the separation profiles for these materials.

Gravimetric wt. % heptane asphaltenes and the total asphaltenes peak areas (cyclohexane plus toluene:methanol (98:2)) are listed in Table 3. The total areas of both the cyclohexane soluble and cyclohexane insoluble asphaltene peaks are plotted against the gravimetric heptane asphaltene content in FIG. 7. ELSD data show a plateau for the severely pyrolyzed oils. This is probably due to the deposition of pre-coke material onto the PTFE stationary phase. This material is not recovered by elution with toluene:methanol (98:2) (v:v). The purpose of the small amount of methanol in this solvent mixture is to minimize the risk of polar normal-phase adsorption effects. Despite this precaution, the PTFE stationary phase in the first inch of the column is stained with a brown colored material after many sample injections, especially if the samples consist of severely pyrolyzed oils. Since the stationary phase is inert PTFE, the material is probably not adsorbed, but rather deposited on the packing. Experiments showed that this brown colored material readily dissolves in methylene chloride. Toluene insoluble pre-coke material is expected to be soluble in solvents with three-dimensional Hansen solubility parameter component values similar to those of methylene chloride, tetrahydrofuran, and quinoline (Table 4) (Hansen 2000). The separation was modified further to add a stronger solvent to dissolve this toluene-insoluble material, to provide a fourth "pre-coke" peak using a solvent with three-dimensional Hansen solubility parameter values near that of methylene chloride. This is described in the following section.

Figure 7:
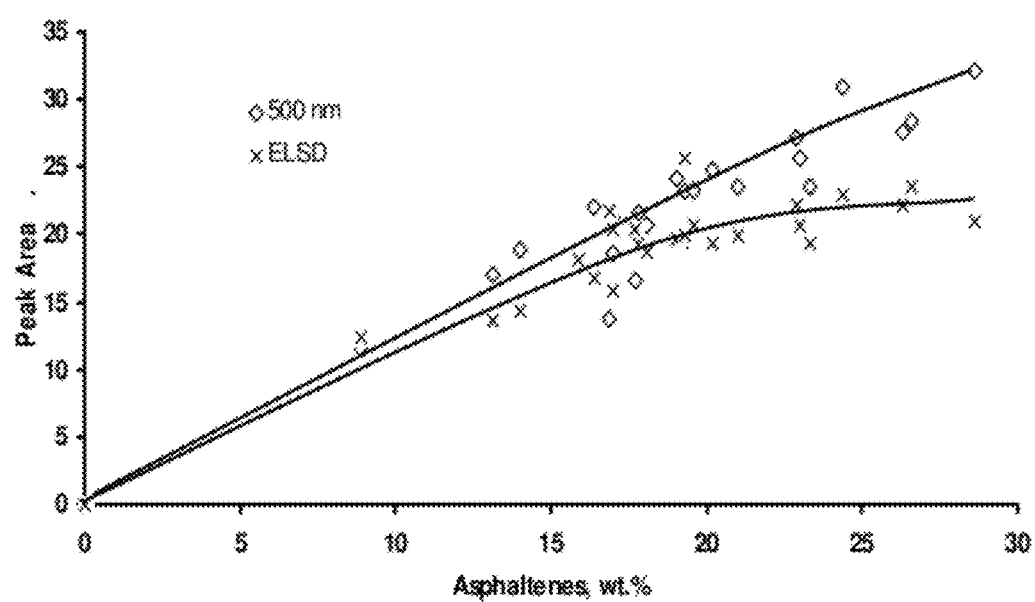
FIG. 7 shows a Correlation of 500 nm Absorbance Detector and ELSD Peak Areas for Three-Solvent Separation with Values from Gravimetric Determination of Heptane Asphaltenes.

The 500 nm peak area show a general correlation with the heptane asphaltene gravimetric data (FIG. 7). The plateau observed with the ELSD for the same separation is still present, but not as evident. This is probably due to the increase in absorptivity for the pyrolyzed asphaltenes material at 500 nm compared with the unpyrolyzed material. Thus, the deposition of a portion of this material onto the stationary phase or loss in the sample filtration step would not be as evident with the optical absorbance detector.

Four Solvent Separation Conditions: The separation conditions that were established for sample analysis using the four solvent system are listed below.

1. 250×10 mm stainless steel column (Alltech 96511)
2. 0.25-0.42 mm PTFE stationary phase
3. Solvent flow rate: 4 mL/min
4. Step gradient times: 0 min. heptane, 15 min. cyclohexane, 30 min. toluene, 40 min. solvent four (cyclohexanone or methylene chloride), 50 min. heptane.
5. Sample solutions: 20 wt. % in cyclohexanone or methylene chloride
6. Amount injected: 10 uL (2 mg)
7. Optical absorbance detector at 500 nm
8. Evaporative light scattering detector (ELSD) at 110° C. and 5 bar nitrogen for cyclohexanone series or 75° C. and 2.5 bar for methylene chloride series Four Solvent Separation Results: From the list of polar solvents with similar Hansen solubility parameters listed in Table 4, two candidate solvents were selected for the four-solvent separation experiments. These were cyclohexanone and methylene chloride. Cyclohexanone does not contain a halogen, and has a boiling point of 155° C., which is much lower than that of Quinoline (237° C.), so it can be used with the ELSD detector. Our observations in the past have been that there are insoluble components present when solutions of asphaltenes are made up in pyridine, so this solvent was not considered. Tetrahydrofuran is known to be unstable and very reactive, so this also was not considered. Methylene chloride has a low boiling point of 40° C., and is a very good solvent for asphaltenes. A disadvantage is that it contains a halogen, and waste solvent from the separation must be disposed of in a halogenated waste stream.

Solutions of 20 wt. % of the original and pyrolyzed residua were prepared in both cyclohexanone and methylene chloride. It takes a minimum of 2 hours for some pyrolyzed samples to fully dissolve in cyclohexanone, even with agitation in an ultrasonic bath. The samples dissolved within 15 minutes in methylene chloride.

Figure 8:
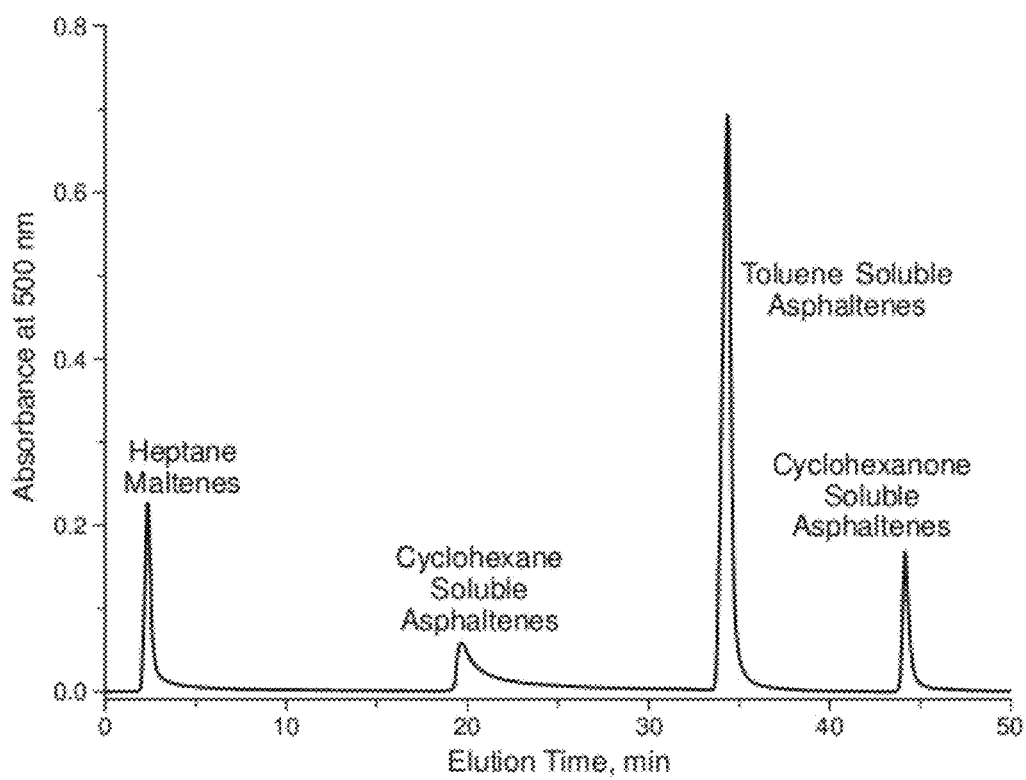
FIG. 8 shows a Separation of 2 mg (10 uL) Unpyrolyzed Boscan Residuum in Cyclohexanone on 250 mm×10 mm PTFE Column, 500 nm Absorbance Detector. Gradient: 0 min. Heptane, 15 min. Cyclohexane, 30 min, Toluene, 40 min. Cyclohexanone, 50 min. Heptane, 4.0 mL/min.
Figure 9:
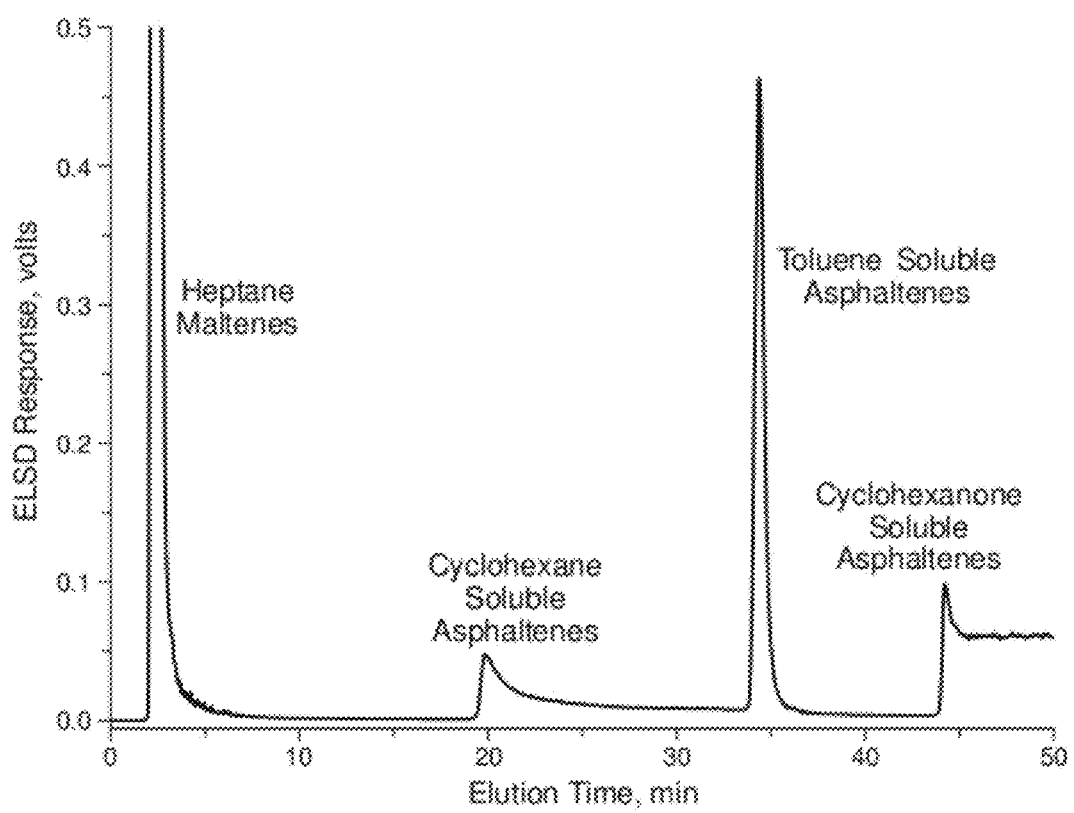
FIG. 9 shows a Separation of 2 mg (10 uL) Unpyrolyzed Boscan Residuum in Cyclohexanone on 250 mm×10 mm PTFE Column, ELSD Detector. Gradient: 0 min. Heptane, 15 min. Cyclohexane, 30 min, Toluene, 40 min. Cyclohexanone, 50 min. Heptane, 4.0 mL/min.

Separation profiles for 10 uL of 20 wt. % unpyrolyzed Boscan residuum in cyclohexanone with cyclohexanone as the fourth solvent using an absorbance detector at 500 nm and an ELSD are provided in FIGS. 8 and 9, respectively. The upward shift of the baseline for the last peak in FIG. 9 is due to the low volatility of cyclohexanone in the ELSD detector. A comparison of the relative peak areas for the three asphaltene peaks (cyclohexane, toluene, and cyclohexanone) are provided in Table 5.

Separation profiles for 10 uL of 20 wt. % unpyrolyzed Boscan residuum in methylene chloride with methylene chloride as the fourth solvent using an absorbance detector at 500 nm and an ELSD are provided in FIGS. 10 and 11, respectively. A comparison of the relative peak areas for the three asphaltene peaks (cyclohexane, toluene, and cyclohexanone) are provided in Table 6.

It is interesting to note that even the unpyrolyzed residua each contain a small portion of the fourth peak, which represents the most polar heptane insoluble material. As pyrolysis progresses, the least polar portion of asphaltenes (cyclohexane soluble) decreases, while the most polar portion (cyclohexanone or methylene chloride soluble) increases (FIGS. 12 and 13). The relative amount of the intermediate polarity material (toluene soluble) drops slowly. Presumably the least polar material passes through a stage of intermediate polarity, which then generates the more polar "pre-coke" material. There is a dramatic increase in the relative amount of the most polar component for the 75-minute pyrolyzed Redwater, B.C. material, as coke begins to form.

The total asphaltenes peak areas are listed in Table 5 for the cyclohexanone separations and in Table 6 for the methylene chloride separations. The total areas of the three asphaltene peaks (cyclohexane soluble, toluene soluble, and cyclohexanone or methylene chloride soluble) are plotted against the gravimetric heptane asphaltene content in FIGS. 14 and 15. As with the three-solvent profile in FIG. 7, the ELSD data show a more severe plateau than the 500 nm data for the severely pyrolyzed oils. This is not due to the deposition of pre-coke material onto the PTFE stationary phase, since the last solvent completely dissolves this material. The plateau profiles in FIGS. 14 and 15 with the ELSD detector indicate that the gravimetric separation of heptane insolubles provides a different result from the on-column precipitation and re-dissolution experiment. The on-column separation provides more detail on the interior structure of the most polar components of residua than a simple gravimetric procedure. The gravimetric separation appears to provide some additional mass which is not accounted for in the on-column separation. The plateau observed with the ELSD for the same separation is not as evident with the 500 nm absorbance detector. This is probably a coincidence which is due to the increase in absorptivity for the pyrolyzed asphaltenes material at 500 nm compared with the unpyrolyzed material. The correlation between asphaltene peak areas and gravimetric asphaltenes content does not take into account the area of the maltenes peaks for the various samples, since with this separation, the maltenes peak is off-scale for 2 mg injections. The use of smaller injections to provide a total peak area (maltenes and asphaltenes) to provide data to correlate with gravimetric asphaltenes content is described in a subsequent section.

A New Stability Gauge: A new parameter that can provide insight into the degree of stability of a petroleum material can be defined from the results of this work. This is the ratio of the peak area for the cyclohexane soluble asphaltenes peak to the cyclohexanone or methylene chloride soluble asphaltenes peak area from the on-column precipitation and re-dissolution profile. The ratios for both solvents using both 500 nm absorbance and ELSD detectors are provided in Table 7. The ratios decrease dramatically with increasing pyrolysis times. Based on these values, threshold values could be established for a particular detector and solvent series used for the separation. The separation could be used as a sensitive tool to diagnose the severity of pyrolysis to which a heavy oil material has been subjected. It also can be used as a rapid means for analyzing samples for refinery distillation process control, to determine the actual "reserve pyrolysis capacity" of a residuum. These numerical results, as with perhaps all numerical results relative to a specific column, are characteristic of a particular PTFE-packed column, and they may vary somewhat for a different PTFE-packed column.

Four Solvent Separation Results With Heptane Asphaltenes: Portions of heptane asphaltenes obtained from the gravimetric procedure were injected onto the column using the four-solvent step gradient procedure, using methylene chloride as the fourth solvent. The amounts injected corresponded to the amounts of asphaltenes that would be present in two milligrams of whole residua sample, based on the gravimetric separation. A blank separation is shown in FIG. 16. The ELSD separation profile for 0.38 mg heptane asphaltenes from unpyrolyzed Boscan residuum is presented in FIG. 17. The ELSD peaks in the blank separation are due to the step gradient solvent changes. As mentioned in the Experimental Section, ELSD peak areas for the blanks were subtracted from the sample areas. The blank corrected sample areas are provided in Table 16. The blank peaks are near in size to some of the sample peaks, which makes an exact calculation of sample areas somewhat difficult. A comparison between the asphaltene peak areas and relative peak areas from whole samples show that the gravimetric asphaltenes peaks in general have a lower total area in Table 8 (gravimetric) than the corresponding total asphaltene peak areas for the whole residua separations listed in Table 6. Also, the gravimetric asphaltenes (Table 8) are relatively deficient in the content of cyclohexane soluble portions relative to the polar materials from the whole sample separations (Table 6). Therefore, the gravimetric and on-column separations provide different results. The gravimetric separation appears to leave more polar material in solution with the maltenes than the on-column separation. This is possibly due to the presence of associated complexes, which retain polar materials in solution during the gravimetric procedure. Possibly the associated complexes are broken apart in solutions with methylene chloride, which are injected on to the PTFE column and precipitated with the heptane mobile phase. Methylene chloride appears to be able to break up the associated complexes efficiently, and the individual molecules are possibly in true solution. As to precipitation, the insoluble molecules appear to coat onto the stationary phase (e.g., see 44 (showing ground PTFE on which precipitated material is coated) and 45 (showing coated lattice)). For solid materials, entropy of solution is not evident. Then, as the molecules coated onto the PTFE surface are exposed to solvents of increasing polarity, they are dissolved from the solid surface based on enthalpic solubility parameter interactions, and they go into solution. Possibly in this case, the separation is based more on an individual molecular level than by associated complexes. This aspect needs to be explored further. If this is the case, the on-column separation provides a more distinct profile of the non-polar and polar material distribution in petroleum materials than does the gravimetric asphaltene procedure. These numerical results are characteristic of a particular PTFE-packed column, and they may vary somewhat for a different PTFE-packed column.

Two Solvent Separation for the Determination of Asphaltenes: To provide a correlation between the on-column precipitation method and gravimetric determination of asphaltenes, separations of methylene chloride solutions of the original and pyrolyzed residua were conducted using a two-solvent step gradient using heptane and methylene chloride. Portions of 0.5 mg of samples were injected to provide both peaks on scale with the ELSD detector (FIG. 18). Small portions of 0.5 mg sample are not useful if the four-solvent separation is used, because the polar peaks are in many cases smaller than the corresponding blank peaks, and quantitation becomes inaccurate. For the two solvent separations, the two peaks are sufficiently large that this is not an issue. The two peaks represent the heptane soluble non-polar material, and all the remaining polar material, which is fully soluble in methylene chloride. Since the ELSD response is based on number of molecules, an area correction is required in order to convert peak area percent into weight percent. This was accomplished by comparing the average response for gravimetric asphaltenes (Table 8) to the average response to gravimetric maltenes (Table 9). The ratio of the two response factors is 1.4, which is approximately related to the ratio of the density of the polar asphaltenes to the density of the maltenes.

Weight percents of polar materials calculated from the two solvent separations using the ELSD detector are listed in Table 9. Weight percents of asphaltenes from the gravimetric procedure are plotted against weight percents of ELSD asphaltenes from the two column separation in FIG. 19. The plot shows that for the particular PTFE-packed column used, there is a critical amount of polar material required, near 18 wt. %, before gravimetric asphaltenes appear. There are four points near the top of the line that are off of the line to the right. These represent the unpyrolyzed and 10-minute pyrolyzed Boscan residuum, and the unpyrolyzed Lloydminster and MaxCL2 residua. The asphaltenes from these materials possibly are highly associated and have significant low polarity salvation shells, so they exhibit enhanced solubility in the gravimetric separation than would be expected from the ELSD correlation line. If these four points, and the points for the three maltenes at y=0 are excluded from linear regression analysis, the correlation coefficient for the line is 0.971, with a slope of 1.24 and a y-intercept of −22.5.

Some Conclusions From Experiments:

Experimental conditions for a new rapid, automated on-column precipitation and re-dissolution method for examining the polar components of original and pyrolyzed residua have been developed. The ratio of ELSD areas of the least polar asphaltene components (cyclohexane soluble) to the most polar components (cyclohexanone or methylene chloride soluble) provides a sensitive indicator of the degree of thermal treatment that the sample has undergone. Total weight percent of polar materials can be determined by a two-solvent method, and the polar material can be further separated into three fractions of increasing polarity using a four-solvent method. Methods based on the new on-column precipitation and re-dissolution separation technique can provide significantly more information about the polar components in petroleum material than the determination of gravimetric asphaltenes. The technique could be scaled up to provide a process for removing the most polar, refractory components from petroleum materials for subsequent processing or use.

TABLE 1

Data for Original Vacuum Residua and Atmospheric Pyrolysis Bottoms

| Residuum | Pyrolysis time @ 400° C., min | Wt. % C7 Asphaltenes | Wt. % CyC6 Sol. | Ks | Wt. % Distillate | Wt % Toluene Insolubles (TI) |
|---|---|---|---|---|---|---|
| Boscan | 0 | 17.7 | 38.5 | 1.6 | na | <0.1 |
| | 10 | 17.8 | 31.6 | 1.5 | 3.9 | <0.1 |
| | 15 | 19.0 | 26.8 | 1.4 | 13.4 | <0.1 |
| | 20 | 20.2 | 28.7 | 1.4 | 10.5 | <0.1 |
| | 35 | 24.4 | 15.4 | 1.2 | 19.5 | <0.1 |
| | 50 | 28.6 | 12.3 | 1.1 | 26.1 | 0.1 |
| | 90 | 16.5 | 6.0 | 1.0 | 39.3 | 23.8 |
| MaxCL2 | 0 | 17.0 | 37.8 | 1.6 | na | <0.1 |
| | 15 | 19.3 | 32.8 | 1.5 | 4.8 | <0.1 |
| | 20 | 23.3 | 21.9 | 1.3 | 5.9 | <0.1 |
| | 35 | 22.9 | 19.5 | 1.2 | 11.7 | <0.1 |
| | 40 | 26.6 | 16.6 | 1.2 | 12.1 | <0.1 |
| | 50 | 26.3 | 15.8 | 1.2 | 16.8 | <0.1 |
| Lloydminster | 0 | 16.9 | 47.7 | 1.9 | na | <0.1 |
| | 15 | 15.9 | 28.6 | 1.4 | 7.6 | <0.1 |
| | 20 | 18.1 | 28.2 | 1.4 | 12.2 | <0.1 |
| | 35 | 19.6 | 16.9 | 1.2 | 16.5 | <0.1 |
| | 40 | 21.0 | 25.4 | 1.3 | 19.5 | <0.1 |
| | 60 | 23.0 | 13.0 | 1.1 | 24.5 | <0.1 |
| Redwater, B.C. | 0 | 8.9 | 37.9 | 1.6 | na | <0.1 |
| | 25 | 13.1 | 27.1 | 1.4 | 6.3 | <0.1 |
| | 35 | 14.0 | 21.6 | 1.3 | 8.2 | <0.1 |
| | 50 | 17.0 | 22.2 | 1.3 | 12.9 | <0.1 |
| | 55 | 16.4 | 19.0 | 1.2 | 13.2 | <0.1 |
| | 75 | 19.3 | 16.0 | 1.2 | 18.7 | 1.1 |

TABLE 2

$K_S$ Data for Original Vacuum Residua and Atmospheric Pyrolysis Bottoms

| Residuum | Pyrolysis time @400° C., min | Weight Percent CyC6 Sol. | $K_S$ | On-Column Three-Solvent Area Percent 500 nm CyC6 Sol. | $K_S$ | ELSD CyC6 Sol. | $K_S$ |
|---|---|---|---|---|---|---|---|
| Boscan | 0 | 37.4 | 1.63 | 28.3, 29.1 | 1.60 | 33.3, 33.1 | 1.50 |
| | 10 | 31.6 | 1.46 | 24.6 | 1.32 | 31.4 | 1.46 |
| | 15 | 26.8 | 1.37 | 20.7 | 1.26 | 26.8 | 1.37 |
| | 20 | 28.7 | 1.40 | 16.8, 18.7 | 1.22 | 21.8, 22.0 | 1.28 |
| | 35 | 15.4 | 1.18 | 9.14 | 1.10 | 17.7 | 1.21 |
| | 50 | 12.3 | 1.14 | 1.57 | 1.02 | 2.0 | 1.02 |
| | 90 (23.8% TI) | 6.0 | 1.0 | — | — | — | — |
| MaxCL2 | 0 | 35.2 | 1.61 | 31.9 | 1.54 | 39.0 | 1.64 |
| | 15 | 32.8 | 1.49 | 20.1 | 1.25 | 25.4 | 1.34 |
| | 20 | 21.9 | 1.28 | 16.1, 17.6 | 1.20 | 20.1, 21.0 | 1.26 |
| | 35 | 19.5 | 1.24 | 12.1 | 1.14 | 20.1 | 1.25 |
| | 40 | 16.6 | 1.20 | 10.5 | 1.12 | 18.2 | 1.22 |
| | 50 | 15.8 | 1.19 | 7.74 | 1.08 | 16.4 | 1.20 |

TABLE 2-continued $K_S$ Data for Original Vacuum Residua and Atmospheric Pyrolysis Bottoms

| Residuum | Pyrolysis time @400° C., min | Weight Percent CyC6 Sol. | $K_S$ | On-Column Three-Solvent Area Percent 500 nm CyC6 Sol. | $K_S$ | ELSD CyC6 Sol. | $K_S$ |
|---|---|---|---|---|---|---|---|
| Lloydminster | 0 | 43.3 | 1.91 | 35.9 | 1.76 | 43.1 | 1.76 |
| | 15 | 28.6 | 1.40 | 23.1 | 1.30 | 31.5 | 1.46 |
| | 20 | 28.2 | 1.39 | 18.0 | 1.22 | 24.6 | 1.33 |
| | 35 | 16.9 | 1.20 | 11.9 | 1.14 | 21.2 | 1.27 |
| | 40 | 25.4 | 1.34 | 11.6 | 1.13 | 21.4 | 1.27 |
| | 60 | 13.0 | 1.15 | 6.30 | 1.07 | 16.4 | 1.20 |
| Redwater, B.C. | 0 | 34.4 | 1.61 | 33.7 | 1.52 | 45.5 | 1.83 |
| | 25 | 27.1 | 1.37 | 21.6 | 1.28 | 33.8 | 1.51 |
| | 35 | 21.6 | 1.28 | 18.4 | 1.22 | 30.0 | 1.43 |
| | 50 | 22.2 | 1.28 | 13.0 | 1.15 | 23.2 | 1.30 |
| | 55 | 19.0 | 1.23 | 12.0 | 1.13 | 22.6 | 1.29 |
| | 75 (1.1% TI) | 16.0 | 1.24 | 8.23 | 1.08 | 21.6 | 1.28 |

TABLE 3

Heptane Asphaltenes Data for Original Vacuum Residua and Atmospheric Pyrolysis Bottoms

| Residuum | Pyrolysis time @ 400° C., min | Weight Percent Asphaltenes | Three-solvent on-column separation Total Asphaltenes Peak Area, counts × $10^6$ 500 nm | ELSD |
|---|---|---|---|---|
| Boscan | 0 | 17.7 | 16.4, 16.9 | 20.3, 20.3 |
| | 10 | 17.8 | 21.5 | 19.3 |
| | 15 | 19.0 | 24.2 | 19.5 |
| | 20 | 20.2 | 24.5, 22.9 | 19.3, 18.0 |
| | 35 | 24.4 | 30.9 | 22.9 |
| | 50 | 28.6 | 32.1 | 20.9 |
| | 90 (23.8% TI) | 16.5 | — | — |
| MaxCL2 | 0 | 17.0 | 18.5 | 20.4 |
| | 15 | 19.3 | 23.2 | 19.8 |
| | 20 | 23.3 | 23.0, 24.1 | 19.3, 20.0 |
| | 35 | 22.9 | 27.1 | 22.1 |
| | 40 | 26.6 | 28.4 | 23.5 |
| | 50 | 26.3 | 27.6 | 22.1 |
| Lloydminster | 0 | 16.9 | 13.7 | 21.7 |
| | 15 | 15.9 | 17.8 | 18.1 |
| | 20 | 18.1 | 20.7 | 18.7 |
| | 35 | 19.6 | 23.3 | 20.6 |
| | 40 | 21.0 | 23.5 | 19.9 |
| | 60 | 23.0 | 25.6 | 20.6 |
| Redwater, B.C. | 0 | 8.9 | 11.6 | 12.4 |
| | 25 | 13.1 | 17.0 | 13.5 |
| | 35 | 14.0 | 18.8 | 14.3 |
| | 50 | 17.0 | 21.3 | 15.8 |
| | 55 | 16.4 | 22.0 | 16.7 |
| | 75 (1.1% TI) | 19.3 | 24.7 | 25.6 |

TABLE 4

Hansen Solubility Parameter Components, $MPa^{1/2}$ (Hansen 2000)

| Solvent | Dispersion | Polar | Hydrogen Bonding |
|---|---|---|---|
| n-Heptane | 15.3 | 0.0 | 0.0 |
| Cyclohexane | 16.8 | 0.0 | 0.2 |
| Toluene | 18.0 | 1.4 | 2.0 |
| Toluene:methanol (98:2)(v:v) | 17.9 | 1.6 | 2.4 |
| Solvents with solubility parameter components similar to methylene chloride | | | |
| Methylene Chloride | 18.2 | 6.3 | 6.1 |
| Cyclohexanone | 17.8 | 6.3 | 5.1 |
| Pyridine | 19.0 | 8.8 | 5.9 |
| Quinoline | 19.4 | 7.0 | 7.6 |
| Tetrahydrofuran | 16.8 | 5.7 | 8.0 |

TABLE 5

On-Column Separation with Four Solvents: Heptane, Cyclohexane, Toluene, and Cyclohexanone

| | Pyrolysis time at 400° C., min. | Total Asphaltenes Peak Area, counts | | Relative Asphaltenes Peak Areas | | | | | |
| | | | | Cyclohexane | | Toluene | | Cyclohexanone | |
| | | 500 nm | ELSD | 500 nm | ELSD | 500 nm | ELSD | 500 nm | ELSD |
|---|---|---|---|---|---|---|---|---|---|
| Boscan | 0 | 18.64 | 22.12 | 0.199 | 0.257 | 0.668 | 0.701 | 0.133 | 0.042 |
| | 10 | 22.76 | 20.09 | 0.143 | 0.179 | 0.685 | 0.762 | 0.171 | 0.059 |

TABLE 5-continued

On-Column Separation with Four Solvents: Heptane, Cyclohexane, Toluene, and Cyclohexanone

| | Pyrolysis time at 400° C., min. | Total Asphaltenes Peak Area, counts | | Relative Asphaltenes Peak Areas | | | | | |
|---|---|---|---|---|---|---|---|---|---|
| | | | | Cyclohexane | | Toluene | | Cyclohexanone | |
| | | 500 nm | ELSD | 500 nm | ELSD | 500 nm | ELSD | 500 nm | ELSD |
| | 15 | 25.25 | 19.34 | 0.106 | 0.143 | 0.680 | 0.761 | 0.214 | 0.096 |
| | 20 | 26.08 | 20.13 | 0.099 | 0.135 | 0.763 | 0.754 | 0.102 | 0.089 |
| | 35 | 29.71 | 19.81 | 0.053 | 0.091 | 0.650 | 0.754 | 0.298 | 0.155 |
| | 50 | 32.47 | 19.35 | 0.030 | 0.065 | 0.611 | 0.748 | 0.359 | 0.187 |
| MaxCL2 | 0 | 20.81 | 19.75 | 0.193 | 0.204 | 0.659 | 0.749 | 0.148 | 0.047 |
| | 15 | 23.74 | 18.21 | 0.104 | 0.107 | 0.699 | 0.802 | 0.198 | 0.091 |
| | 20 | 25.17 | 19.44 | 0.091 | 0.091 | 0.700 | 0.819 | 0.209 | 0.091 |
| | 35 | 27.21 | 19.85 | 0.060 | 0.066 | 0.695 | 0.809 | 0.245 | 0.124 |
| | 40 | 28.70 | 21.47 | 0.055 | 0.068 | 0.682 | 0.792 | 0.263 | 0.139 |
| | 50 | 29.64 | 20.70 | 0.040 | 0.053 | 0.666 | 0.792 | 0.295 | 0.155 |
| Lloydminster | 0 | 16.13 | 21.85 | 0.214 | 0.239 | 0.650 | 0.728 | 0.136 | 0.033 |
| | 15 | 19.08 | 16.02 | 0.114 | 0.123 | 0.696 | 0.806 | 0.190 | 0.071 |
| | 20 | 21.70 | 17.19 | 0.088 | 0.097 | 0.705 | 0.811 | 0.207 | 0.092 |
| | 35 | 23.00 | 16.98 | 0.064 | 0.067 | 0.693 | 0.813 | 0.243 | 0.120 |
| | 40 | 24.92 | 18.89 | 0.057 | 0.076 | 0.683 | 0.780 | 0.260 | 0.144 |
| | 60 | 25.69 | 17.44 | 0.035 | 0.040 | 0.670 | 0.807 | 0.295 | 0.154 |
| Redwater, B.C. | 0 | 14.99 | 9.77 | 0.174 | 0.187 | 0.657 | 0.764 | 0.169 | 0.049 |
| | 25 | 19.01 | 10.29 | 0.091 | 0.095 | 0.688 | 0.810 | 0.221 | 0.094 |
| | 35 | 20.59 | 11.32 | 0.074 | 0.096 | 0.685 | 0.794 | 0.241 | 0.110 |
| | 50 | 23.36 | 11.65 | 0.060 | 0.083 | 0.670 | 0.796 | 0.271 | 0.121 |
| | 55 | 23.12 | 14.55 | 0.051 | 0.057 | 0.660 | 0.795 | 0.290 | 0.148 |
| | 75 (coke) | 26.13 | 12.93 | 0.038 | 0.038 | 0.643 | 0.774 | 0.320 | 0.188 |

TABLE 6

On-Column Separation of 2.0 mg Portions of Whole Residua with Four Solvents: Heptane, Cyclohexane, Toluene, and Methylene Chloride

| | Pyrolysis time at 400° C., min. | Total Asphaltenes Peak Area, counts | | Relative Asphaltenes Peak Areas | | | | | |
|---|---|---|---|---|---|---|---|---|---|
| | | | | Cyclohexane | | Toluene | | $CH_2Cl_2$ | |
| | | 500 nm | ELSD | 500 nm | ELSD | 500 nm | ELSD | 500 nm | ELSD |
| Boscan | 0 | 21.41 | 23.97 | 0.096 | 0.151 | 0.810 | 0.788 | 0.094 | 0.060 |
| | 10 | 23.71 | 19.68 | 0.068 | 0.122 | 0.797 | 0.783 | 0.135 | 0.095 |
| | 15 | 28.45 | 21.29 | 0.050 | 0.099 | 0.775 | 0.767 | 0.175 | 0.099 |
| | 20 | 27.53 | 20.95 | 0.045 | 0.098 | 0.776 | 0.768 | 0.179 | 0.134 |
| | 35 | 29.35 | 19.73 | 0.021 | 0.067 | 0.720 | 0.726 | 0.259 | 0.206 |
| | 50 | 31.87 | 20.25 | 0.017 | 0.046 | 0.680 | 0.699 | 0.302 | 0.254 |
| MaxCL2 | 0 | 19.50 | 18.90 | 0.085 | 0.130 | 0.786 | 0.790 | 0.130 | 0.080 |
| | 15 | 24.19 | 18.94 | 0.049 | 0.083 | 0.769 | 0.778 | 0.182 | 0.139 |
| | 20 | 27.16 | 21.66 | 0.043 | 0.088 | 0.764 | 0.761 | 0.192 | 0.151 |
| | 35 | 26.67 | 19.64 | 0.027 | 0.062 | 0.732 | 0.739 | 0.241 | 0.199 |
| | 40 | 29.82 | 22.38 | 0.024 | 0.054 | 0.700 | 0.718 | 0.276 | 0.228 |
| | 50 | 27.66 | 19.32 | 0.017 | 0.038 | 0.693 | 0.714 | 0.290 | 0.248 |
| Lloydminster | 0 | 15.31 | 20.82 | 0.090 | 0.146 | 0.808 | 0.793 | 0.102 | 0.061 |
| | 15 | 17.21 | 14.99 | 0.044 | 0.071 | 0.790 | 0.809 | 0.166 | 0.119 |
| | 20 | 18.24 | 15.17 | 0.033 | 0.068 | 0.770 | 0.785 | 0.197 | 0.147 |
| | 35 | 18.91 | 14.84 | 0.023 | 0.057 | 0.738 | 0.754 | 0.239 | 0.189 |
| | 40 | 21.42 | 16.76 | 0.023 | 0.052 | 0.714 | 0.732 | 0.263 | 0.216 |
| | 60 | 21.46 | 15.46 | 0.017 | 0.039 | 0.698 | 0.721 | 0.285 | 0.240 |
| Redwater, B.C. | 0 | 15.64 | 12.66 | 0.084 | 0.107 | 0.757 | 0.798 | 0.141 | 0.096 |
| | 25 | 17.03 | 13.17 | 0.036 | 0.145 | 0.757 | 0.710 | 0.206 | 0.145 |
| | 35 | 17.49 | 11.68 | 0.029 | 0.062 | 0.740 | 0.757 | 0.231 | 0.182 |
| | 50 | 20.03 | 13.45 | 0.024 | 0.052 | 0.709 | 0.729 | 0.266 | 0.219 |
| | 55 | 18.48 | 11.63 | 0.022 | 0.041 | 0.695 | 0.720 | 0.283 | 0.239 |
| | 75 (coke) | 16.04 | 10.30 | 0.018 | 0.020 | 0.650 | 0.630 | 0.332 | 0.450 |

TABLE 7

Ratio of Areas of the Cyclohexane Soluble Asphaltene Peaks to the Cyclohexanone-Soluble or Methylene Chloride-Soluble Asphaltene Peaks

| | | On-Column Precipitation and Re-dissolution Peak Area Ratios | | | |
|---|---|---|---|---|---|
| | | Cyclohexane/ Cyclohexanone | | Cyclohexane/ Methylene Chloride | |
| | Pyrolysis time at 400° C., min. | 500 nm | ELSD | 500 nm | ELSD |
| Boscan | 0 | 1.50 | 6.11 | 1.02 | 2.52 |
| | 10 | 0.84 | 3.02 | 0.51 | 1.29 |
| | 15 | 0.49 | 1.49 | 0.28 | 0.74 |
| | 20 | 0.46 | 1.32 | 0.25 | 0.73 |
| | 35 | 0.18 | 0.58 | 0.08 | 0.33 |
| | 50 | 0.08 | 0.35 | 0.06 | 0.18 |
| MaxCL2 | 0 | 1.30 | 4.38 | 0.65 | 1.62 |
| | 15 | 0.52 | 1.17 | 0.27 | 0.60 |
| | 20 | 0.44 | 1.00 | 0.23 | 0.59 |
| | 35 | 0.24 | 0.53 | 0.11 | 0.31 |
| | 40 | 0.21 | 0.49 | 0.09 | 0.24 |
| | 50 | 0.14 | 0.34 | 0.06 | 0.15 |
| Lloydminster | 0 | 1.58 | 7.25 | 0.88 | 2.40 |
| | 15 | 0.60 | 1.74 | 0.27 | 0.60 |
| | 20 | 0.42 | 1.06 | 0.17 | 0.46 |
| | 35 | 0.26 | 0.56 | 0.10 | 0.30 |
| | 40 | 0.22 | 0.53 | 0.09 | 0.24 |
| | 60 | 0.12 | 0.26 | 0.06 | 0.16 |
| Redwater, B.C. | 0 | 1.03 | 3.81 | 0.60 | 1.12 |
| | 25 | 0.41 | 1.01 | 0.18 | 1.00 |
| | 35 | 0.31 | 0.88 | 0.12 | 0.34 |
| | 50 | 0.22 | 0.68 | 0.09 | 0.24 |
| | 55 | 0.17 | 0.38 | 0.08 | 0.17 |
| | 75 (coke) | 0.12 | 0.27 | 0.05 | 0.06 |

TABLE 8

On-Column Separation of Gravimetric Heptane Asphaltenes with Four Solvents: Heptane, Cyclohexane, Toluene, and Methylene Chloride using ELSD Detector

| | Pyrolysis time at 400° C., min. | Total Asphaltene mg[a] | Peak Area | Response Factor Area/mg | Relative Asphaltenes Peak Areas | | | |
|---|---|---|---|---|---|---|---|---|
| | | | | | Heptane | Cyclohexane | Toluene | $CH_2Cl_2$ |
| Boscan | 0 | 0.36 | 13.44 | 37.3 | <0.001 | 0.027 | 0.788 | 0.185 |
| | 15 | 0.38 | 11.48 | 30.2 | <0.001 | 0.031 | 0.752 | 0.217 |
| | 35 | 0.49 | 13.94 | 28.4 | <0.001 | 0.011 | 0.661 | 0.328 |
| | 50 | 0.57 | 14.25 | 25.0 | 0.072 | 0.026 | 0.549 | 0.354 |
| MaxCL2 | 0 | 0.34 | 13.85 | 40.7 | <0.001 | 0.019 | 0.761 | 0.220 |
| | 15 | 0.39 | 15.14 | 38.8 | <0.001 | 0.034 | 0.674 | 0.291 |
| | 35 | 0.46 | 16.75 | 36.4 | <0.001 | 0.041 | 0.632 | 0.327 |
| | 50 | 0.52 | 18.11 | 34.8 | 0.052 | 0.017 | 0.578 | 0.353 |
| Lloydminster | 0 | 0.34 | 13.83 | 40.7 | <0.001 | 0.025 | 0.794 | 0.181 |
| | 15 | 0.32 | 13.86 | 43.3 | <0.001 | 0.036 | 0.731 | 0.233 |
| | 35 | 0.40 | 15.57 | 38.9 | <0.001 | 0.035 | 0.685 | 0.281 |
| | 60 | 0.46 | 18.15 | 39.5 | 0.053 | 0.033 | 0.603 | 0.312 |
| Redwater, B.C. | 0 | 0.18 | 8.88 | 49.3 | <0.001 | 0.027 | 0.685 | 0.288 |
| | 35 | 0.28 | 13.66 | 48.8 | <0.001 | 0.020 | 0.663 | 0.318 |
| | 55 | 0.33 | 16.13 | 48.9 | <0.001 | 0.016 | 0.635 | 0.348 |
| | 75 | 0.38 | 19.79 | 52.1 | 0.059 | 0.020 | 0.558 | 0.363 |
| | Average response, area/mg | | | 39.6 | | | | |
| | Relative standard deviation | | | 19.6% | | | | |

[a] Corresponds to the amount of gravimetric asphaltenes in 2.0 mg residuum

TABLE 9

On-Column Separation of 0.50 mg of Whole Residua and Residua Heptane
Maltenes with Two Solvents: Heptane and Methylene Chloride using
ELSD Detector

|  | Pyrolysis time at 400° C., min. | Peak Area Counts Maltenes | Peak Area Counts Asphaltenes | Total Area | Response Area/mg | ELSD Response Corrected (×1.4) Asphaltene Weight Percent |
|---|---|---|---|---|---|---|
| Boscan | 0 | 16.85 | 7.49 | 24.34 | 48.7 | 38.4 |
|  | 10 | 17.77 | 7.18 | 24.95 | 49.9 | 36.1 |
|  | 15 | 17.71 | 6.89 | 24.60 | 49.2 | 35.3 |
|  | 20 | 18.36 | 7.40 | 25.76 | 51.5 | 36.1 |
|  | 35 | 19.08 | 8.32 | 27.40 | 54.8 | 37.9 |
|  | 50 | 18.80 | 8.72 | 27.52 | 55.0 | 39.4 |
| MaxCL2 | 0 | 21.57 | 8.50 | 30.07 | 60.1 | 35.6 |
|  | 15 | 21.09 | 8.03 | 29.12 | 58.2 | 34.8 |
|  | 20 | 20.44 | 8.02 | 28.46 | 56.9 | 35.5 |
|  | 35 | 19.76 | 8.03 | 27.79 | 55.6 | 36.3 |
|  | 40 | 18.03 | 8.36 | 26.39 | 52.8 | 39.4 |
|  | 50 | 19.54 | 9.06 | 28.60 | 57.2 | 39.4 |
| Lloydminster | 0 | 19.19 | 7.77 | 26.96 | 53.9 | 36.2 |
|  | 15 | 20.88 | 6.55 | 27.43 | 54.9 | 30.5 |
|  | 20 | 20.06 | 7.23 | 27.29 | 54.6 | 33.5 |
|  | 35 | 20.09 | 7.14 | 27.23 | 54.5 | 33.2 |
|  | 40 | 20.74 | 8.13 | 28.87 | 57.7 | 35.4 |
|  | 60 | 21.02 | 8.70 | 29.72 | 59.4 | 36.7 |
| Redwater, B.C. | 0 | 19.53 | 4.86 | 24.39 | 48.8 | 25.8 |
|  | 25 | 19.52 | 5.52 | 25.04 | 50.1 | 28.3 |
|  | 35 | 18.75 | 5.56 | 24.31 | 48.6 | 29.3 |
|  | 50 | 19.63 | 6.50 | 26.13 | 52.3 | 31.2 |
|  | 55 | 20.70 | 6.36 | 27.06 | 54.1 | 30.1 |
|  | 75 (coke) | 20.48 | 7.19 | 27.67 | 55.3 | 33.0 |
|  | Average response, area/mg |  |  |  | 53.9 |  |
|  | Relative standard deviation |  |  |  | 3.5% |  |
| Unpyrolyzed Maltenes |  |  |  |  |  |  |
| Boscan |  | 24.37 | 3.04 | 27.41 | 54.8 | 14.9 |
| Lloydminster |  | 22.39 | 5.06 | 27.45 | 54.9 | 24.0 |
| Redwater, B.C. |  | 25.96 | 4.58 | 30.54 | 61.1 | 19.8 |
|  | Average response, area/mg |  |  |  | 56.9 |  |
|  | Relative standard deviation |  |  |  | 3.6% |  |

Additional Information: As can be easily understood from the foregoing, the basic concepts of the present invention may be embodied in a variety of ways. It involves both analysis and processing techniques as well as devices to accomplish the appropriate analysis or processing. In this application, the analysis and processing techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this non-provisional application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims that will be included in any subsequent patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon when drafting the claims for any subsequent patent application. It should be understood that such language changes and broader or more detailed claiming may be accomplished at a later date (such as by any required deadline) or in the event the applicant subsequently seeks a patent filing based on this filing. With this understanding, the reader should be aware that this disclosure is to be understood to support any subsequently filed patent application that may seek examination of as broad a base of claims as deemed within the applicant's right and may be designed to yield a patent covering numerous aspects of the invention both independently and as an overall system.

Further, each of the various elements of the invention and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "container" should be understood to encompass disclosure of the act of "containing"—whether explicitly discussed or not—and, conversely, were there effectively disclosure of the act of "containing", such a disclosure should be understood to encompass disclosure of a "container" and even a "means for containing" Such changes and alternative terms are to be understood to be explicitly included in the description.

Any acts of law, statutes, regulations, or rules mentioned in this application for patent; or patents, publications, or other references mentioned in this application for patent are hereby incorporated by reference. Any priority case(s) claimed by this application is hereby appended and hereby incorporated by reference, to the extent the priority case is not inconsistent with the disclosure in this non-provisional application. In addition, as to each term used it should be understood that unless its utilization in this application is inconsistent with a broadly supporting interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the list of references in the information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

Thus, the applicant(s) should be understood to have support to claim and make a statement of invention to at least: i) each of the analytical/processing devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) the various combinations and permutations of each of the elements disclosed, and xii) each potentially dependent claim or concept as a dependency on each and every one of the independent claims or concepts presented.

In addition and as to computer aspects and each aspect amenable to programming or other electronic automation, the applicant(s) should be understood to have support to claim and make a statement of invention to at least: xii) processes performed with the aid of or on a computer as described throughout the above discussion, xiv) a programmable apparatus as described throughout the above discussion, xv) a computer readable memory encoded with data to direct a computer comprising means or elements which function as described throughout the above discussion, xvi) a computer configured as herein disclosed and described, xvii) individual or combined subroutines and programs as herein disclosed and described, xviii) the related methods disclosed and described, xix) similar, equivalent, and even implicit variations of each of these systems and methods, xx) those alternative designs which accomplish each of the functions shown as are disclosed and described, xxi) those alternative designs and methods which accomplish each of the functions shown as are implicit to accomplish that which is disclosed and described, xxii) each feature, component, and step shown as separate and independent inventions, and xxiii) the various combinations and permutations of each of the above.

With regard to claims whether now or later presented for examination, it should be understood that for practical reasons and so as to avoid great expansion of the examination burden, the applicant may at any time present only initial claims or perhaps only initial claims with only initial dependencies. Support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible.

Finally, any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

What is claimed is:

1. A method comprising the steps of:
providing a vessel having a substantially chemically inert stationary phase established therein and having at least one vessel inlet, said substantially chemically inert stationary phase forming a fixed bed in said vessel;
inputting a precipitant solvent into said vessel through at least one vessel inlet;
inputting a hydrocarbonaceous material into said vessel through at least one vessel inlet;
intentionally precipitating asphaltenes within said vessel and in the presence of said substantially chemically inert stationary phase, wherein said substantially chemically inert stationary phase is substantially chemically inert relative to said asphaltenes such that substantially all said precipitated asphaltenes do not adsorb onto said substantially chemically inert stationary phase;
generating a remnant liquid upon performing said step of intentionally precipitating said asphaltenes;
inputting a material dissolving solvent into said vessel through at least one vessel inlet; and
dissolving at least a portion of said asphaltenes with said material dissolving solvent to generate a dissolved material solution.

2. A method as described in claim 1 wherein said step of inputting a hydrocarbonaceous material into said vessel through at least one vessel inlet comprises the step of inputting a hydrocarbon sample into said vessel.

3. A method as described in claim 2 wherein said step of inputting a hydrocarbon sample into said vessel through at least one vessel inlet comprises the step of inputting oil into said vessel.

4. A method as described in claim 2 wherein said step of inputting a hydrocarbon sample into said vessel through at least one vessel inlet comprises the step of inputting a wax component of oil into said vessel.

5. A method as described in claim 2 wherein said step of inputting a hydrocarbon sample into said vessel through at least one vessel inlet comprises the step of inputting an asphaltene into said vessel.

6. A method as described in claim 2 wherein said step of inputting a hydrocarbonaceous material into said vessel through at least one vessel inlet further comprises the step of inputting a sample in solution into said vessel.

7. A method as described in claim 2 wherein said substantially chemically inert stationary phase is also substantially chemically inert relative to said sample.

8. A method as described in claim 1 wherein said step of inputting a hydrocarbonaceous material into said vessel through at least one vessel inlet comprises the step of inputting oil into said vessel.

9. A method as described in claim 1 wherein said step of inputting a precipitant solvent into said vessel through at least one vessel inlet comprises the step of inputting into said vessel a precipitant solvent selected from the group consisting of low polarity solvents, low polarity solvent mixtures, aliphatic solvents, heptane, pentane and isooctane.

10. A method as described in claim 1 wherein said step of generating a remnant liquid comprises the step of generating a remnant solution.

11. A method as described in claim 2 further comprising the step of determining at least one characteristic of said hydrocarbon sample.

12. A method as described in claim 11 wherein said step of determining at least one characteristic of said sample comprises the step of using a technique selected from the group consisting of evaporative light scattering, mass spectrometry, optical absorbance, x-ray, conductivity, oxidation/reduction, refractive index, polarimetry, atomic spectroscopy, and fluorescence.

13. A method as described in claim 11 wherein said step of determining at least one characteristic of said sample comprises the step of analyzing said remnant liquid.

14. A method as described in claim 11 wherein said step of determining at least one characteristic of said sample comprises the step of determining a weight percentage of asphaltenes.

15. A method as described in claim 11 wherein said step of determining at least one characteristic of said sample comprises the step of analyzing said dissolved material solution.

16. A method as described in claim 11 wherein said step of determining at least one characteristic of said sample comprises the step of determining a mass fraction of heptane asphaltenes soluble in cyclohexane.

17. A method as described in claim 11 wherein said step of determining at least one characteristic of said sample comprises the step of determining at least two characteristics of said sample.

18. A method as described in claim 16 wherein said step of determining at least two characteristics of said sample comprises the step of determining a cyclohexane soluble peak value and a methylene chloride soluble peak value.

19. A method as described in claim 1 wherein said step of inputting a material dissolving solvent comprises the step of inputting a material dissolving solvent selected from the group consisting of solvents having a higher polarity than that of said precipitant solvent, solvent mixtures having a higher polarity than that of said precipitant solvent, naphthenic oils, aromatic oils, ketones, halogenated solvents, cyclohexane, toluene, cyclohexanone, and methylene chloride.

20. A method as described in claim 1 further comprising the step of separating said remnant liquid from said asphaltenes.

21. A method as described in claim 1 further comprising the step of removing said remnant liquid from said vessel.

22. A method as described in claim 20 further comprising the step of replacing said remnant liquid with said material dissolving solvent.

23. A method as described in claim 1 further comprising the step of eluting said dissolved material solution from said vessel.

24. A method as described in claim 1 wherein said step of inputting a material dissolving solvent into said vessel comprises the step of inputting cyclohexane, or a different solvent or solvent mixture with substantially the same polarity as cyclohexane.

25. A method as described in claim 1 wherein said step of dissolving at least a portion of said asphaltenes with said material dissolving solvent comprises the step of dissolving only a first portion of said asphaltenes with said material dissolving solvent.

26. A method as described in claim 25 further comprising the step of inputting a second material dissolving solvent into said vessel through at least one vessel inlet to dissolve at least a second portion of said asphaltenes.

27. A method as described in claim 26 wherein said step of inputting a second material dissolving solvent into said vessel comprises the step of inputting a stronger material dissolving solvent.

28. A method as described in claim 27 wherein said step of inputting a stronger material dissolving solvent into said vessel comprises the step of inputting into said vessel solvent that gradually increases in strength.

29. A method as described in claim 28 wherein said step of inputting into said vessel solvent that gradually increases in strength is performed during continuous solvent flow.

30. A method as described in claim 27 wherein said strengths of said material dissolving solvents do not change in a step gradient fashion.

31. A method as described in claim 27 wherein said strengths of said material dissolving solvents change in a step gradient fashion.

32. A method as described in claim 25 further comprising the step of inputting increasingly stronger material dissolving solvent into said vessel to dissolve at least a second portion of said asphaltenes and generate a second dissolved material solution.

33. A method as described in claim 32 wherein said step of inputting increasingly stronger material dissolving solvent comprises the step of inputting material dissolving solvent that gradually increases in strength.

34. A method as described in claim 33 wherein said step of step of inputting material dissolving solvent that gradually increases in strength is performed during continuous solvent flow.

35. A method as described in claim 32 where input solvent strengths do not change in a step gradient fashion.

36. A method as described in claim 26 further comprising the step of replacing said dissolved material solution with said second material dissolving solvent.

37. A method as described in claim 26 wherein said step of inputting a second material dissolving solvent into said vessel comprises the step of inputting toluene, or a different solvent or solvent mixture with substantially the same polarity as toluene.

38. A method as described in claim 32 further comprising the steps of analyzing said second dissolved material solution.

39. A method as described in claim 32 wherein said step of inputting increasingly stronger material dissolving solvent into said vessel to dissolve at least a second portion of said asphaltenes comprises the step of inputting increasingly stronger material dissolving solvent into said vessel to dissolve said second and at least a third portion of said asphaltenes.

40. A method as described in claim 39 further comprising the step of generating a third dissolved material solution.

41. A method as described in claim 39 wherein said step of inputting increasingly stronger material dissolving solvent into said vessel comprises the step of inputting methylene chloride or a solvent or solvent mixture with substantially the same polarity as methylene chloride.

42. A method as described in claim 40 further comprising the step of analyzing said third dissolved material solution.

43. A method as described in claim 1 further comprising the step of fractionating said solution into at least two parts.

44. A method as described in claim 1 wherein each of said steps is started in the order in which it appears.

45. A method as described in claim 1 wherein said step of providing a vessel having a substantially chemically inert stationary phase established therein comprises the step of providing a vessel having established therein a stationary phase selected from the group of: oligomers of PTFE, polymers of PTFE, polyphenylene sulfide, fluorinated polymers, silicon polymer and PEEK.

46. A method as described in claim 1 wherein said step of providing a vessel having a substantially chemically inert stationary phase established therein comprises the step of providing a column having a substantially chemically inert stationary phase established therein.

47. A method as described in claim 46 wherein said step of providing a column comprises the step of providing a column that is part of a chromatograph.

48. A method as described in claim 1 wherein said step of providing a vessel having a substantially chemically inert stationary phase established therein comprises the step of providing a batch type vessel having a substantially chemically inert stationary phase established therein.

49. A method as described in claim 1 wherein said step of intentionally precipitating asphaltenes within said vessel comprises the step of intentionally precipitating solid material.

50. A method as described in claim 1 wherein said step of intentionally precipitating asphaltenes within said vessel comprises the step of intentionally precipitating gel or viscous liquid.

51. A method as described in claim 1 wherein said method is accomplished, at least in part, with a flow system.

52. A method as described in claim 51 wherein said flow system is a continuous flow system.

53. A method as described in claim 1 wherein said step of inputting a precipitant solvent into said vessel through at least one vessel inlet comprises the step of inputting a liquid into said vessel through at least one vessel inlet.

54. A method as described in claim 1 wherein said step of inputting a precipitant solvent into said vessel through at least one vessel inlet comprises the step of inputting gel or viscous liquid.

55. A method as described in claim 1 wherein said method is a method selected from the group consisting of coking onset estimation method, oil processing method; oil fractionating method, oil production method, pipeline fouling related method, hydrotreating, distillation method, vacuum distillation method, atmospheric distillation method, visbreaking method, blending method, asphalt formation method, asphalt extraction method, and asphaltene content of oil measurement method.

56. A method as described in claim 1 wherein said method is an automated method.

57. A refinery or apparatus in which the method of claim 1 is performed.

58. A refinery that processes hydrocarbons based on analysis results generated, at least in part, upon performance of the method of claim 1.

59. A product produced by a process that is based on analysis results generated, at least in part, upon performance of the method of claim 1.

60. Controlling, designing or monitoring processing of a hydrocarbon through use of information generated from the method of claim 1.

61. A method as described in claim 1 further comprising the step of determining a concentration of an asphaltene fraction of said hydrocarbonaceous material.

62. A method as described in claim 11 wherein said step of determining at least one characteristic of said sample comprises the step of monitoring a concentration of an asphaltene fraction of said sample.

63. A method as described in claim 27 further comprising the step of generating a solubility profile of asphaltenes of said hydrocarbonaceous material.

64. A method as described in claim 27 further comprising the step of measuring relative concentrations of asphaltene fractions of said hydrocarbonaceous material.

65. A method as described in claim 1 further comprising the step of determining at least one solubility parameter for said hydrocarbonaceous material.

66. A method as described in claim 1 further comprising the step of determining at least one asphaltene stability parameter.

67. A method as described in claim 66 wherein said step of determining at least one asphaltene stability parameter comprises the step of determining a coking index.

68. A method as described in claim 1 further comprising the step of improving the efficiency of a distillation process by monitoring an asphaltene stability parameter.

69. A method as described in claim 68 wherein said step of improving the efficiency of a distillation process by monitoring an asphaltene stability parameter comprises the step of improving the efficiency of a distillation process by monitoring a coking index.

70. A method as described in claim 1 further comprising the step of reducing pipeline fouling in a refinery by a hydrocarbon being processed, in part through the use of information gained, at least in part, upon performance of the method of claim 1.

71. A method comprising the steps of:
providing a vessel having a substantially chemically inert stationary phase established therein and having at least one vessel inlet, said substantially chemically inert stationary phase forming a fixed bed in said vessel;
inputting a precipitant solvent into said vessel through at least one vessel inlet;
inputting a hydrocarbonaceous material into said vessel through at least one vessel inlet;
intentionally precipitating asphaltenes within said vessel and in the presence of said substantially chemically inert stationary phase, wherein said substantially chemically inert stationary phase is substantially chemically inert relative to said asphaltenes such that substantially all said precipitated asphaltenes do not adsorb onto said substantially chemically inert stationary phase;
generating a remnant liquid upon performing said step of intentionally precipitating said asphaltenes;
inputting a material dissolving solvent into said vessel through at least one vessel inlet;
dissolving at least a portion of said asphaltenes with said material dissolving solvent to generate a dissolved material solution;
determining at least one characteristic of said hydrocarbonaceous material; and
reducing pipeline fouling in a refinery by a hydrocarbon being processed, in part through the use of said at least one characteristic, wherein said step of reducing fouling comprises the steps of controlling a process to minimize the fouling tendency of product hydrocarbons and monitoring the formation of pre-coke material in said product hydrocarbons downstream of a distillation unit.

72. A method as described in claim 71 wherein said step of monitoring the formation of pre-coke material comprises the step of monitoring the formation of methylene chloride:methanol soluble asphaltenes.

73. A method comprising the steps of:
providing a vessel having a substantially chemically inert stationary phase established therein and having at least one vessel inlet, said substantially chemically inert stationary phase forming a fixed bed in said vessel;
inputting a precipitant solvent into said vessel through at least one vessel inlet;
inputting a hydrocarbonaceous material into said vessel through at least one vessel inlet;
intentionally precipitating asphaltenes within said vessel and in the presence of said substantially chemically inert stationary phase, wherein said substantially chemically inert stationary phase is substantially chemically inert relative to said asphaltenes such that substantially all said precipitated asphaltenes do not adsorb onto said substantially chemically inert stationary phase;
generating a remnant liquid upon performing said step of intentionally precipitating said asphaltenes;
inputting a material dissolving solvent into said vessel through at least one vessel inlet;
dissolving at least a portion of said asphaltenes with said material dissolving solvent to generate a dissolved material solution;
determining at least one characteristic of said hydrocarbonaceous material; and
reducing pipeline fouling in a refinery by a hydrocarbon being processed, in part through the use of said at least one characteristic,
wherein said step of reducing fouling comprises the steps of controlling a process to minimize the fouling tendency of product hydrocarbons,
said method further comprising the step of heating, in a distillation unit, a hydrocarbon being processed therein based on observed formation of pre-coke material.

74. A method as described in claim 1 wherein said step of providing a vessel having a substantially chemically inert stationary phase established therein comprises the step of providing a vessel having a substantially chemically inert, polymeric stationary phase established therein.

75. A method as described in claim 11 wherein said step of determining at least one characteristic of said hydrocarbon sample comprises the step of using a detector.

* * * * *